(12) United States Patent
Li et al.

(10) Patent No.: US 10,517,961 B2
(45) Date of Patent: Dec. 31, 2019

(54) DRUG FORMULATION BASED ON PARTICULATES COMPRISING POLYSACCHARIDE-VITAMIN CONJUGATE

(71) Applicant: ZY Therapeutics, Inc., Cary, NC (US)

(72) Inventors: Jun Li, Cary, NC (US); Jian Bao, Cary, NC (US); Wei Wang, Cary, NC (US)

(73) Assignee: ZY Therapeutics, Inc., Cary, NC (US)

( * ) Notice: Subject to any disclaimer, the term of this patent is extended or adjusted under 35 U.S.C. 154(b) by 0 days.

(21) Appl. No.: 15/745,066

(22) PCT Filed: Sep. 25, 2016

(86) PCT No.: PCT/US2016/053626
§ 371 (c)(1),
(2) Date: Jan. 15, 2018

(87) PCT Pub. No.: WO2017/053920
PCT Pub. Date: Mar. 30, 2017

(65) Prior Publication Data
US 2018/0193483 A1 Jul. 12, 2018

Related U.S. Application Data

(60) Provisional application No. 62/233,112, filed on Sep. 25, 2015.

(51) Int. Cl.
| | |
|---|---|
| *A61K 47/69* | (2017.01) |
| *A61K 31/337* | (2006.01) |
| *A61K 31/4745* | (2006.01) |
| *A61K 47/61* | (2017.01) |
| *A61K 47/54* | (2017.01) |
| *A61P 35/00* | (2006.01) |
| *A61K 45/06* | (2006.01) |

(52) U.S. Cl.
CPC ........ *A61K 47/6921* (2017.08); *A61K 31/337* (2013.01); *A61K 31/4745* (2013.01); *A61K 45/06* (2013.01); *A61K 47/545* (2017.08); *A61K 47/61* (2017.08); *A61P 35/00* (2018.01); *A61K 2300/00* (2013.01)

(58) Field of Classification Search
None
See application file for complete search history.

(56) References Cited

U.S. PATENT DOCUMENTS

| | | | |
|---|---|---|---|
| 6,159,502 | A | 12/2000 | Russell-Jones et al. |
| 2002/0192235 | A1 | 12/2002 | Chalasani et al. |
| 2011/0166079 | A1* | 7/2011 | Vitek .......... C07K 14/775 514/19.4 |
| 2012/0231069 | A1 | 9/2012 | Nowotnik et al. |
| 2015/0018540 | A1 | 1/2015 | Prakash et al. |

FOREIGN PATENT DOCUMENTS

| | | |
|---|---|---|
| CN | 103992417 A | 8/2014 |
| WO | 2011130716 A2 | 10/2011 |
| WO | 2012030745 A1 | 3/2012 |
| WO | 2015126841 A1 | 8/2015 |

OTHER PUBLICATIONS

Zu, Int. J. Mol. Sci. 2011, 12, 4237-4249.*
Hao, International Journal of Pharmaceutics 444 (2013) 77-84.*
Li, CN 103992417 A, Aug. 20, 2014, machine translation.*
Varshosaz, BioMed Research International, vol. 2013, Article ID 680712, pp. 1-16.*
Nayebsadrian, Journal of Nanomaterials, vol. 2012, Article ID 860691, pp. 1-7.*
International Search Report & Written Opinion dated Dec. 6, 2016, regarding PCT/US2016/053626.
International Preliminary Report on Patentability dated Mar. 27, 2018, regarding PCT/US2016/053626.
Extended European search report in the European Patent Application No. 16849831.9, dated Mar. 29, 2019.

* cited by examiner

*Primary Examiner* — Layla D Berry
(74) *Attorney, Agent, or Firm* — Intellectual Valley Law, P.C.

(57) ABSTRACT

The present disclosure provides formulations for pharmacologically active reagents, including formulations based on particulates formed from a biodegradable polymer (e.g., a polysaccharide such as dextran) linked to a vitamin or related agent (e.g., folic acid). Hydrophobic pharmaceutically active agents (such as anti-cancer drugs, e.g., paclitaxel) are encapsulated into the polysaccharide-vitamin conjugate for the administration of paclitaxel. The active agent is in a core portion of the particulate, instead of on the surface of the particulate. Processes for making and using the particulates and compositions comprising the same are also disclosed. In particular, methods of cancer diagnosis and treatment are provided.

24 Claims, 8 Drawing Sheets

DRUG FORMULATION BASED ON PARTICULATES COMPRISING POLYSACCHARIDE-VITAMIN CONJUGATE

CROSS-REFERENCE TO RELATED APPLICATION

This application is a national stage application under 35 U.S.C. § 371 of International Application No. PCT/US2016/053626, filed Sep. 25, 2016, which claims priority to U.S. Provisional Patent Application No. 62/233,112, filed Sep. 25, 2015, the contents of which are incorporated by reference in the entirety.

TECHNICAL FIELD

The present disclosure generally relates to compounds, drug compositions, formulations and delivery systems for pharmacologically active reagents, including anti-cancer therapeutics. In some aspects, the present disclosure relates to compositions comprising a modified polysaccharide, a therapeutic reagent, and a nanocarrier. In some aspects, the present disclosure relates to methods of making the compounds, drug compositions, and formulations, and methods of using the same, for example, in cancer treatment.

BACKGROUND

Most of the clinically used anti-cancer drugs, such as paclitaxel, docetaxel, doxorubicin, have poor water solubility. Often these drugs cannot be directly administered, e.g., parenterally, to patients. For example, paclitaxel and many of its derivatives and analogues have exceedingly low solubility in most physiologically acceptable aqueous solvents that would be compatible with intravascular administration. Thus, a surfactant as an excipient is often necessary to facilitate in vivo delivery of the effective compound. For example, Taxotere® (Sanofi-Aventis) is a formulation of docetaxel with polysorbate 80 as the excipient, along with ethanol and citric acid. The paclitaxel formulation Taxol® (Bristol-Myers Squibb) is formulated using Cremophor® EL, a polyoxyethylated castor oil. This formulation contains 50% (v/v) alcohol, as well as an 88-fold excess of Cremophor® EL, which has a potential for inducing serious side effects. The acute and common clinical side effects of the paclitaxel formulation are severe: listing dyspnea, hypotension, angioedema, generalized urticaria, and most notably anaphylactoid reactions, with risk for a fatal outcome. In addition, the high Cremophor® EL concentrations facilitate the leaking of "plasticizers," i.e., chemicals used in the manufacture of disposable infusion bags and tubing sets into the infusate. The long-term risks of patient exposure to these chemicals are unknown. Thus, the excipients in these drug formulations may lead to serious side effects, such as allergy, renal toxicity, nerve and heart toxicity, and in certain cases, has mandated premedication with diphenhydramine, $H_2$-antagonists, and even corticosteroids.

Accordingly, there is need for alternative drug compositions and formulations of anti-cancer drugs, in order to alleviate dangerous side effects and provide a more even drug supply for both conventional dose therapy and for high dose chemotherapy. The present disclosure addresses the need.

SUMMARY

In one aspect, the present disclosure provides a particulate comprising a plurality of polysaccharide-vitamin conjugates; and an active agent encapsulated in the plurality of polysaccharide-vitamin conjugates; wherein each of the plurality of polysaccharide-vitamin conjugates comprises a polysaccharide molecule and one or more molecules of vitamin or analogue or derivative covalently conjugated to the polysaccharide molecule through a linker group; the active agent is non-covalently bound to a molecule of vitamin or analogue or derivative thereof.

Optionally, a surface of the particulate is substantially hydrophilic.

Optionally, the active agent is in a core portion of the particulate.

Optionally, the polysaccharide molecule is conjugated to each of the one or more molecules of a vitamin or analogue or derivative thereof through a linker molecule comprising a first chemical group reactive to one or more functional groups on the polysaccharide molecule or a functionalized polysaccharide molecule, and a second chemical group reactive to one or more functional groups on each of the one or more molecules of a vitamin or analogue or derivative or a functionalized molecule thereof.

Optionally, the polysaccharide-vitamin conjugate comprises a first vitamin or analogue or derivative thereof and a second vitamin or analogue or derivative thereof different from the first vitamin or analogue or derivative thereof, the first vitamin or analogue or derivative thereof and the second vitamin or analogue or derivative thereof are covalently linked to the polysaccharide at different positions of the polysaccharide, respectively.

Optionally, the vitamin is folate, cholic acid, nicotinamide, N,N-diethylnicotinamide, biotin, or sodium salicylate.

Optionally, the polysaccharide is a polysaccharide soluble in water and in an organic solvent.

Optionally, the polysaccharide is dextran or derivative thereof, cellulose or derivative thereof, carboxymethylcellulose, or hyaluronic acid or derivative thereof.

Optionally, the polysaccharide is succinylated, carboxymethylated, and/or modified by cyclic anhydride.

Optionally, the one or more molecules of vitamin or analogue or derivative are hydrophobic.

Optionally, the active agent is hydrophobic.

Optionally, the active agent is an anti-neoplastic agent.

Optionally, the active agent is a taxane compound or analogue thereof or a camptothecin compound or analogue thereof.

Optionally, an average diameter of the particulate is between about 20 nm and about 1000 nm.

In another aspect, the present disclosure provides a pharmaceutical composition comprising a particulate described herein, and a pharmaceutically acceptable carrier or excipient.

Optionally, the composition is formulated as a tablet, a capsule, a powder, or a liquid.

Optionally, the pharmaceutical composition further comprises a suitable solvent or a pharmaceutically-acceptable injection vehicle.

Optionally, the pharmaceutical composition is formulated as a solution, an emulsion, a suspension, or a colloid.

Optionally, the pharmaceutical composition is sterilized by passing through a membrane of an average pore size of about 0.2 μm.

Optionally, the particulate or composition described herein is configured for administration in a subject via the topical, enteral/gastrointestinal, parenteral, epidural, intracerebral, intracerebroventrical, intradermal, subcutaneous, nasal, oral, intravenous, intraarterial, intramuscular, intraosseous infusion, intravitreal, intravesical, transdermal, or transmucosal route.

In another aspect, the present disclosure provides a method for treating a subject, comprising administering to a subject in need thereof an effective amount of the particulate or composition described herein.

Optionally, the active agent is an anti-neoplastic agent.

Optionally, the active agent is a taxane compound or analogue thereof or a camptothecin compound or analogue thereof Optionally, encapsulating the active agent in the particulate does not substantially change the subject's responsiveness to a given amount of the active agent.

Optionally, the active agent is a cytotoxic agent, and the subject's responsiveness is measured by cytotoxicity of the cytotoxic agent.

Optionally, the method increases the tolerance dose of the subject to the active agent, compared to administering the active agent not encapsulated in the particulate.

Optionally, the subject has a cancer or a neoplastic disease or condition.

Optionally, the cancer is non-small cell lung cancer or a breast cancer cell.

Optionally, administering to the subject an effective amount of the particulate or composition described herein reduces growth of neoplastic cells in the subject.

In another aspect, the present invention provides a method for inhibiting growth of a cell, comprising delivering to a cell an effective amount of the particulate or composition described herein.

Optionally, the cell is a cancer cell.

Optionally, the cell is a non-small cell lung cancer cell or a breast cancer cell.

In another aspect, the present invention provides a method for reducing tumor growth in a subject, comprising treating a subject in need thereof with an effective amount of radiation, and treating the subject with an effective amount of the particulate or composition described herein.

In another aspect, the present invention provides a method for reducing tumor growth in a subject, comprising treating a subject in need thereof with an effective amount of a chemotherapeutic agent, and treating the subject with an effective amount of the particulate or composition described herein.

In another aspect, the present invention provides a method for reducing tumor growth in a subject, comprising treating a subject in need thereof with an effective amount of a biologically active therapeutic, and treating the subject with an effective amount of the particulate or composition described herein.

Optionally, the active agent is a therapeutic agent or a diagnostic agent.

In one aspect, disclosed herein is a particulate (e.g., a microparticle) having a shell-core structure, comprising: a shell comprising a polysaccharide-vitamin conjugate, the polysaccharide-vitamin conjugate comprising one or more molecules of a vitamin or analogue or derivative thereof covalently linked to a polysaccharide; and a core comprising an active agent entrapped in the shell, wherein the one or more molecules of a vitamin or analogue or derivative thereof are located between the core and the polysaccharide.

In one embodiment, the polysaccharide is conjugated to each of the one or more molecules of a vitamin or analogue or derivative thereof through a linker molecule comprising a first chemical group reactive to one or more functional groups on the polysaccharide, and a second chemical group reactive to one or more functional groups on each of the one or more molecules of a vitamin or analogue or derivative thereof.

In one embodiment, the polysaccharide-vitamin conjugate comprises a first vitamin or analogue or derivative thereof and a second vitamin or analogue or derivative thereof different from the first vitamin or analogue or derivative thereof; the first vitamin or analogue or derivative thereof and the second vitamin or analogue or derivative thereof are covalently linked to the polysaccharide at different positions of the polysaccharide, respectively.

In one embodiment, one or more molecules of a vitamin or analogue or derivative thereof can be located on the inner surface of the shell of a particulate (e.g., a microparticle) of the present disclosure. In any of the embodiments disclosed herein, the vitamin can be folate, nicotinamide, N,N-diethylnicotinamide, biotin, or sodium salicylate. In another embodiment, the vitamin can be modified. In any of the embodiments disclosed herein, the vitamin can be modified by amination.

In one embodiment, the polysaccharide is a polysaccharide soluble in an organic solvent.

In one aspect, the polysaccharide can be dextran or derivative thereof, cellulose or derivative thereof, carboxymethylcellulose, or hyaluronic acid or derivative thereof, in a particulate (e.g., a microparticle) of the present disclosure. In another aspect, the one or more molecules of a vitamin or analogue or derivative thereof can be covalently linked to the polysaccharide via a linker group, in any of the embodiments disclosed herein. The linker may be or comprise a disulfide bond, an ester linkage, a γ-glutamyl-ε-lysine bond, and/or a diazo-linkage. In yet another embodiment, the polysaccharide can be succinylated, carboxymethylated, and/or modified by cyclic anhydride.

In any of the embodiments disclosed herein, preferably, the active agent is hydrophobic. In one aspect, the active agent can be an anti-neoplastic agent, for example, an anti-cancer drug. In another aspect, the active agent can be paclitaxel or derivative thereof, docetaxel or derivative thereof, or doxorubicin or derivative thereof. In yet another aspect, the active agent is not covalently linked to the polysaccharide-vitamin conjugate.

In any of the embodiments disclosed herein, a particulate of the present disclosure can be a microparticle. In any of the embodiments disclosed herein, a particulate of the present disclosure can be a nanoparticle. In certain aspects, an average diameter of the particulate can be between about 20 nm to about 1000 nm, e.g., 20 nm to 100 nm, 100 nm to 200 nm, 100 nm to 400 nm, or 400 nm to 1000 nm. In certain aspects, an average diameter of the particulate can be between about 20 nm and about 200 nm. In certain other aspects, an average diameter of the particulate can be between about 20 nm and about 50 nm, between about 50 nm and about 100 nm, between about 100 nm and about 150 nm, or between about 150 nm and about 200 nm.

Also disclosed herein is a composition comprising a particulate (e.g., a microparticle) having a shell-core structure, the particulate comprising: a shell comprising a polysaccharide-vitamin conjugate, the polysaccharide-vitamin conjugate comprising one or more molecules of a vitamin or analogue or derivative thereof covalently linked to a polysaccharide; and a core comprising an active agent entrapped in the shell, wherein the one or more molecules of a vitamin or analogue or derivative thereof are located between the core and the polysaccharide.

In certain embodiments, the polysaccharide is conjugated to each of the one or more molecules of a vitamin or analogue or derivative thereof through a linker molecule comprising a first chemical group reactive to one or more functional groups on the polysaccharide, and a second chemical group reactive to one or more functional groups on each of the one or more molecules of a vitamin or analogue or derivative thereof.

In certain embodiments, the polysaccharide-vitamin conjugate comprises a first vitamin or analogue or derivative thereof and a second vitamin or analogue or derivative thereof different from the first vitamin or analogue or derivative thereof; the first vitamin or analogue or derivative thereof and the second vitamin or analogue or derivative thereof are covalently linked to the polysaccharide at different positions of the polysaccharide, respectively.

In certain embodiments, the one or more molecules of a vitamin or analogue or derivative thereof can be located on the inner surface of the shell. In certain embodiments, the one or more molecules of a vitamin or analogue or derivative thereof are not located on the outer surface of the shell. In certain other embodiments, the vitamin can be folate, nicotinamide, N,N-diethylnicotinamide, biotin, or sodium salicylate. In certain aspects, the vitamin can be a modified vitamin. In any of the embodiments disclosed herein, the vitamin can be modified by amination.

In certain embodiments, the polysaccharide is a polysaccharide soluble in an organic solvent.

In any of the embodiments disclosed herein, the polysaccharide of the composition can be dextran or derivative thereof, cellulose or derivative thereof, carboxymethylcellulose, or hyaluronic acid or derivative thereof. In one aspect, the one or more molecules of a vitamin or analogue or derivative thereof of the composition disclosed herein can be covalently linked to the polysaccharide via a linker group, which may comprise a disulfide bond, an ester linkage, a γ-glutamyl-ε-lysine bond, and/or a diazo-linkage. In one embodiment, the polysaccharide can be succinylated, carboxymethylated, and/or modified by cyclic anhydride.

In any of the embodiments of the composition disclosed herein, the active agent can be hydrophobic. In one aspect, the active agent can be an anti-neoplastic agent, e.g., an anti-cancer drug. In another aspect, the active agent can be paclitaxel or derivative thereof, docetaxel or derivative thereof, or doxorubicin or derivative thereof. In yet another aspect, the active agent is not covalently linked to the polysaccharide-vitamin conjugate.

In any of the embodiments disclosed herein, a particulate of the present disclosure can be a microparticle. In any of the embodiments of the composition disclosed herein, the particulate can be a nanoparticle. In certain aspects, an average diameter of the particulate can be between about 20 nm to about 1000 nm, e.g., 20 nm to 100 nm, 100 nm to 200 nm, 100 nm to 400 nm, or 400 nm to 1000 nm. In certain aspects, an average diameter of the particulate can be between about 20 nm and about 200 nm. In certain other aspects, an average diameter of the particulate can be between about 20 nm and about 50 nm, between about 50 nm and about 100 nm, between about 100 nm and about 150 nm, or between about 150 nm and about 200 nm.

In any of the embodiments disclosed herein, the composition can further comprise a pharmaceutically acceptable carrier or excipient. In one aspect, the composition can be formulated as a tablet, a capsule, a powder, or a liquid. In another aspect, the composition may further comprise a suitable solvent or a pharmaceutically-acceptable injection vehicle. In particular embodiments, the composition can be formulated as a solution, an emulsion, a suspension, or a colloid. In certain aspects, the composition can be sterilized by passing through a membrane of an average pore size of about 0.2 μm, or be sterilized by other sterilization processes. In certain aspects, the particulate (e.g., a microparticle) or composition can be sterilized by filtration, radiation, heating, or ethylene oxide treatment, or any combination thereof in any suitable order. In preferred embodiments, passing through the membrane and other sterilization processes do not substantially change the particle size of the particulates. In other preferred embodiments, the sterilization methods keep the particulate size less than about 200 nm.

In any of the embodiments disclosed herein, the composition can further comprise a cryoprotectant. In particular embodiments, the cryoprotectant can be a sugar. In certain embodiments, the sugar can be sucrose or trehalose.

In any of the embodiments disclosed herein, the composition may be subjected to lyophilization. In one aspect, the average diameter of the particulate (e.g., a microparticle) is substantially unchanged during or after lyphilization, and the particulate does not aggregate during the lyphilization process, after lyphilization, or after reconstitution. In one embodiment, the average diameter of the particulate (e.g., a microparticle) is less than about 200 nm during the lyphilization process, after lyphilization, or after reconstitution, and the particulate does not aggregate during the lyphilization process, after lyphilization, or after reconstitution. In other preferred embodiments, the lyphilization process keeps the particulate size less than about 200 nm. In any of the embodiments disclosed herein, the composition can be formulated as a lyophilized powder or lyo-cake in a container for subsequent re-suspension or dissolution of the composition in a pharmaceutically-acceptable carrier or excipient.

In any of the preceding embodiments, the particulate (e.g., a microparticle) or composition of the present disclosure can be configured for administration in a subject via the topical, enteral/gastrointestinal, parenteral, epidural, intracerebral, intracerebroventrical, intradermal, subcutaneous, nasal, oral, intravenous, intraarterial, intramuscular, intraosseous infusion, intravitreal, intravesical, transdermal, or transmucosal route.

A process for preparing a composition comprising the particulate (e.g., a microparticle) of any of the preceding embodiments is also disclosed. In one aspect, the process comprises: providing a polysaccharide-vitamin conjugate comprising one or more molecules of a vitamin or analogue or derivative thereof covalently linked to a polysaccharide; combining the polysaccharide-vitamin conjugate and the active agent in a suitable solvent, or combining a solution of the polysaccharide-vitamin conjugate and a solution of the active agent; and subjecting the mixture of the polysaccharide-vitamin conjugate and the active agent to a high sheer homogenizer to form a composition comprising a particulate (e.g., a microparticle) comprising the polysaccharide-vitamin conjugate and the active agent, wherein the active agent is entrapped in a shell formed by the polysaccharide-vitamin conjugate and the one or more molecules of a vitamin or analogue or derivative thereof are located between the active agent and the polysaccharide.

In particular aspects, the mixture of the polysaccharide-vitamin conjugate and the active agent can be subjected to a high sheer homogenizer under a pressure in the range of about 10,000 to about 30,000 psi (pounds per square inch). In certain embodiments, the solution of the polysaccharide-vitamin conjugate and the solution of the active agent are immiscible. In any of the embodiments disclosed herein, combining the solution of the polysaccharide-vitamin conjugate and the solution of the active agent can result in an emulsion, for example, a microemulsion.

In any of the embodiments of the process disclosed herein, the process can further comprise isolating the particulate (e.g., a microparticle) by diafiltration, filtration, solvent evaporation, or centrifugation, or any combination thereof in any suitable order. In any of the preceding embodiments, the process can further comprise isolating the particulate (e.g., a microparticle) by addition of a co-solvent followed by diafiltration. In certain aspects, the co-solvent can be deionized water. In any of the preceding embodiments, the process can further comprise a purifying step and/or a sterilizing step. In certain aspects, the purifying step and/or the sterilizing step can comprise washing the particulate with a suitable solvent, and/or filtering the particulate through a membrane of an average pore size of 0.2 µm. In any of the preceding embodiments, the process can further comprise a drying step and/or a lyophilization step in the presence of a cryoprotectant. In particular embodiments, the lyophilization step does not substantially aggregate the particulate or substantially change the average diameter of the particulate. In one embodiment, the average diameter of the particulate is less than about 200 nm, and remains less than about 200 nm during the lyphilization process, after lyphilization, or after reconstitution. In any of the embodiments disclosed herein, the composition after the lyophilization step can be formulated as a lyo-cake or lyophilized powder.

Also disclosed herein is the product of any of the preceding embodiments of the processes.

The present disclosure also provides a method for treating a subject, comprising administering to the subject an effective amount of the particulate (e.g., a microparticle) or composition of any of the embodiments disclosed herein. In one aspect, the active agent comprised in the particulate or composition can be an anti-neoplastic agent. In particular embodiments, the active agent can be paclitaxel or derivative thereof, docetaxel or derivative thereof, or doxorubicin or derivative thereof. In certain aspects, entrapping the active agent in the particulate does not substantially change the subject's responsiveness to a given amount of the active agent. In other aspects, the active agent can be a cytotoxic agent, and the subject's responsiveness can be measured by cytotoxicity of the cytotoxic agent. In other aspects, the method for treating a subject increases the tolerance dose of the subject to the active agent, compared to administering the active agent not entrapped in a particulate of the present disclosure.

In any of the embodiments of the method disclosed herein, the subject may have a cancer or a neoplastic disease or condition, or a neoplastic syndrome. In particular embodiments, the cancer can be non-small cell lung cancer or breast cancer. In certain aspects, administering to the subject an effective amount of the particulate (e.g., a microparticle) or composition can reduce growth of neoplastic cells in the subject.

The present disclosure also provides a method for inhibiting growth of a cell, comprising delivering to a cell an effective amount of the particulate (e.g., a microparticle) or composition of any of the embodiments disclosed herein. In one embodiment, the cell can be a cancer cell. In one aspect, the cell can be a non-small cell lung cancer cell.

The present disclosure additionally provides a method for reducing tumor growth in a subject, comprising treating a subject with an effective amount of a combination of radiation and the particulate (e.g., a microparticle) or composition of any of the embodiments disclosed herein. Also provided is a method for reducing tumor growth in a subject, comprising treating a subject in need thereof with an effective amount of radiation, and treating the subject with an effective amount of the particulate or composition of any of the embodiments disclosed herein.

In certain other aspects, provided herein is a method for reducing tumor growth in a subject, comprising treating a subject with an effective amount of a combination of a chemotherapeutic agent and the particulate (e.g., a microparticle) or composition of any of the embodiments disclosed herein. Also provided is a method for reducing tumor growth in a subject, comprising treating a subject in need thereof with an effective amount of a chemotherapeutic agent, and treating the subject with an effective amount of the microparticle or composition of any of the embodiments disclosed herein.

In yet other aspects, a method for reducing tumor growth in a subject is disclosed, the method comprising treating a subject with an effective amount of a combination of a biologically active therapeutic agent and the particulate (e.g., a microparticle) or composition of any of the embodiments disclosed herein. Also provided is a method for reducing tumor growth in a subject, comprising treating a subject in need thereof with an effective amount of a biologically active therapeutic agent, and treating the subject with an effective amount of the microparticle or composition of any of the embodiments disclosed herein.

In any of the embodiments for the particulate, composition, process, product, or method disclosed herein, the active agent entrapped in the particulate can be a therapeutic agent or a diagnostic agent.

BRIEF DESCRIPTION OF THE FIGURES

The following drawings are merely examples for illustrative purposes according to various disclosed embodiments and are not intended to limit the scope of the present invention.

FIG. 1 illustrates the preparation of a formulation according to certain embodiments of the present disclosure.

FIG. 5 illustrates the preparation of a formulation according to certain embodiments of the present disclosure.

DETAILED DESCRIPTION

Figure 1A:
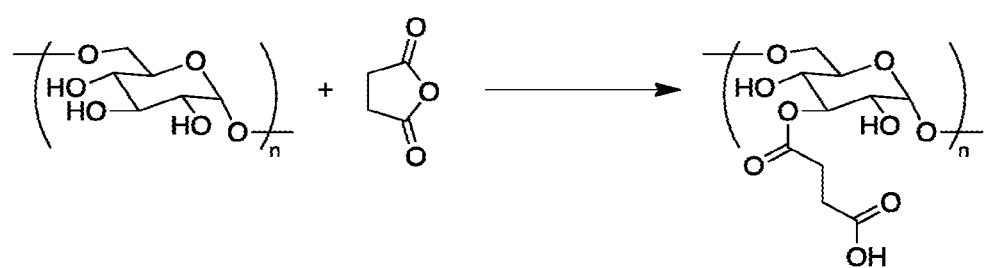
FIG. 1A is a schematic showing the synthesis of succinylated 1, 6 dextran.

A detailed description of one or more embodiments of the claimed subject matter is provided below along with accompanying figures that illustrate the principles of the claimed subject matter. The claimed subject matter is described in connection with such embodiments, but is not limited to any embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure or manner. These details provided herein are for the purpose of example and the claimed subject matter may be practiced according to the claims without some or all of these specific details. It is to be understood that other embodiments can be used and structural changes can be made without departing from the scope of the claimed subject matter. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

All publications, including patent documents, scientific articles and databases, referred to in this application and the bibliography and attachments are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The practice of the provided embodiments will employ, unless otherwise indicated, conventional techniques and descriptions of organic chemistry, polymer chemistry and technology (in particular, polysaccharide chemistry and technology), molecular biology, cell biology, and biochemistry, which are within the skill of those who practice in the art. Such techniques include polysaccharide synthesis and/or modification, and preparation of particulates, microparticles, including nanoparticles. Specific illustrations of suitable techniques can be had by reference to the examples herein. However, other equivalent conventional procedures can, of course, also be used. Such conventional techniques and descriptions can be found in standard laboratory manuals such as Starch: Chemistry and Technology, 2nd Edition, Ed. Whistler, BeMiller, and Paschall, Academic Press, 1984, and Methods in Carbohydrate Chemistry, Vol. IV, Ed. Whistler, Academic Press, 1964, both of which are herein incorporated in their entirety by reference for all purposes. U.S. Pat. No. 5,977,348, U.S. Patent Application No. 20130149385, and U.S. Pat. No. 6,689,338 also disclose methods of polysaccharide synthesis and/or modification, or preparation of particulates (e.g., microparticles). All three patent publications are herein incorporated in their entirety by reference for all purposes.

As used herein and in the appended claims, the singular forms "a," "an," and "the" include plural referents unless the context clearly dictates otherwise. For example, "a" or "an" means "at least one" or "one or more." Thus, reference to "a sugar" can refer to one or more type of sugars, and reference to "the method" includes reference to equivalent steps and methods disclosed herein and/or known to those skilled in the art, and so forth.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se.

As used herein, an "individual" can be any living organism, including humans and other mammals. A "subject" as used herein can be an organism to which the provided compositions, methods, kits, devices, and systems can be administered or applied. In one embodiment, the subject can be a mammal or a cell, a tissue, an organ or a part of the mammal. Mammals include, but are not limited to, humans, and non-human animals, including farm animals, sport animals, rodents and pets. In certain aspects of the present disclosure, a biological sample or material can be obtained and used, and can refer to any sample or material obtained from a living or viral source or other source of macromolecules and biomolecules, and includes any cell type or tissue of a subject from which nucleic acid or protein or other macromolecules can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

As used herein, a "composition" can be any mixture of two or more products or compounds. It may be a solution, a suspension, liquid, powder, a paste, aqueous, non-aqueous or any combination thereof.

The terms "poorly water-soluble" or "hydrophobic" can refer to water solubility of less than about 30 mg/ml, less than about 10 mg/mL, or less than about 1 mg/mL at ambient temperature and pressure and at about pH 7. For example, this may correspond to vitamins, polysaccharide-vitamin conjugates, and/or therapeutic agents which are to be characterized by the commonly used terms "sparingly soluble," "slightly soluble," "very slightly soluble," "practically insoluble" and "insoluble," all of which are used herein interchangeably.

As used herein, "biological activity" may include the in vivo activities of a compound or composition or physiological responses that result upon in vivo administration of a compound, composition or other mixture. Biological activity, thus, may encompass therapeutic effects and pharmaceutical activity of such compounds, compositions or mixtures. Biological activities may be observed in vitro systems designed to test or use such activities.

The term "binding" can refer to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. Proteins that form stable complexes with other molecules are often referred to as receptors while their binding partners are called ligands.

A vitamin or vitamin moiety, as used herein, may refer to a vitamin and related agents, derivatives thereof, and analogues thereof, all of which possess or substantially retain the desired function or activity of the vitamin, depending on the context. Similarly, a polysaccharide or polysaccharide moiety may refer to a polysaccharide, derivatives thereof, analogues thereof, and other related agents that possess or substantially retain the desired function or activity of the polysaccharide, depending on the context.

As used herein, the term "linker molecule" refers to a molecule having a first chemical group reactive to one or more functional groups on the polysaccharide, and a second chemical group reactive to one or more functional groups on a vitamin or analogue or derivative thereof. Optionally, the linker molecule further includes at least one atom between the first chemical group and the second chemical group. Optionally, the linker molecule further includes a spacer between the first chemical group and the second chemical group.

Chemotherapy has been one of the major approaches to the control and cure of cancers. In many cases of conventional cancer chemotherapy, it is often necessary to increase the quantity of cytotoxic agents administered in an exponential fashion in order to obtain a linear increase in the killing of cancer cells. An undesirable increase in non-specific cytotoxicity of bystander, healthy cells often exacerbate the patient's overall condition. In many cases, it is often necessary to repeatedly deliver smaller doses of cytotoxin, which inevitably leads to the survival of a small fraction of drug-resistant cells. In addition, nonselective action on cells other than cancerous cells by cytotoxic drugs still remains a major problem.

Particulates Encapsulating Active Agents

In one aspect, the present disclosure provides a particulate comprising a plurality of polysaccharide-vitamin conjugates and an active agent encapsulated in the plurality of polysaccharide-vitamin conjugates. In some embodiments, each of the plurality of polysaccharide-vitamin conjugates includes a polysaccharide molecule and one or more molecules of vitamin or analogue or derivative covalently conjugated to the polysaccharide molecule through a linker group. The active agent is non-covalently bound to a molecule of vitamin or analogue or derivative thereof.

In some embodiments, the surface of the particulate is substantially hydrophilic. For example, the particulate may include a surface having substantially hydrophilic polysaccharide molecules whereas the active agent is encapsulated inside the particulate, i.e., the active agent is not exposed on the surface of the particulate but buried underneath the surface. In some examples, the polysaccharide-vitamin conjugates self-assemble into the particulate, with the active agents non-covalently bound to the conjugates during the self-assembling process. In some conjugates, the polysaccharide moiety is hydrophilic, the vitamin moiety is hydrophobic, and the polysaccharide-vitamin conjugates are amphiphilic molecules, which self-assemble into the particulates. The self-assembling process minimizes the water-conjugate interfacial free energy, with the substantially hydrophilic surface as a stabilizing interface between a core portion of the particulate and external aqueous environment such as body fluids. Underneath the substantially hydrophilic surface, the conjugate molecules assemble together, e.g., via hydrophobic interactions between the hydrophobic moieties of the conjugate. Optionally, the conjugate molecules in the core portion of the particulate are arranged in a random fashion, i.e., lacking any definite structure features such as a bi-layer structure. Accordingly, the active agents may be randomly encapsulated throughout the core portion of the particulate. For example, in some particulates of the present disclosure, the active agents do not necessarily segregate inside an inner core of the particulate. Thus, reference to a core-shell structure in the present disclosure generally refers to a particulate structure having a substantially hydrophilic surface and a core portion in which the active agents are encapsulated in any fashion. It was discovered that the present particulates have a surprisingly large loading capacity of the active agents (e.g., up to about 30% w/w or more loading capacity). In some particulates, the core portion of the particulate has a substantially homogeneous structure, i.e., lacking an obvious segregation of active agents, hydrophobic moieties, and hydrophilic moieties into separate or distinct sub-portions. As a result, an outstanding loading capacity may be achieved in the present particulate.

The particulates may be made into various appropriate sizes. In some embodiments, the particulates have an average diameter in the range of 20 nm to 1000 nm, e.g., 20 nm to 100 nm, 100 nm to 200 nm, 100 nm to 400 nm, or 400 nm to 1000 nm. Optionally, the particulate is a microparticle. Optionally, the particulate is a nanoparticle.

In some embodiments, the particulates have a loading capacity of about 10% w/w to about 30% w/w loading capacity, e.g., about 15% w/w to about 30%, about 20% w/w to about 30% w/w, or about 25% w/w to about 30% w/w loading capacity.

Optionally, the active agent is a hydrophobic drug. Optionally, the hydrophobic active agent is non-covalently associated with a hydrophobic moiety of the conjugate molecule (e.g., the vitamin moiety). In some particulates, the hydrophobic moieties and any associated active agents are randomly or substantially homogeneously distributed throughout the particulate.

In certain aspects, targeting agents such as monoclonal antibodies to "tumor-specific antigens" may be used, either alone or in combination with other strategies, for examples, those using the particulates (e.g., microparticles) or compositions disclosed herein, in order to increase the dose of cytotoxic agents delivered to cancer cells. In many instances however, when used alone, monoclonal antibodies to "tumor-specific antigens" may still not be able to deliver enough cytotoxic agents coupled to antibodies for effective cancer cell killing.

In 2005, FDA approved a human albumin bound paclitaxel formulation (Abraxane®) for advanced metastatic breast cancer. The formulation increases the clinic dose of paclitaxel, reduces side effects compared to previous formulations, and increases patient survival rate. Paclitaxel formulations on the market and related clinical trials are summarized in Table 1. In some aspects, biodegradable polymers can be used to reduce the risk of contamination, for example, by viruses from donated blood, of human albumin.

in the form of a particulate. In one embodiment, dextran is conjugated with folic acid, and the dextran-folic acid conjugates and the paclitaxel molecules are assembled into the particulate. The hydrophobic drug, paclitaxel, is encapsulated in a core portion of the particulate. In certain aspects, the vitamin (e.g., folic acid) can be modified to increase the hydrophobicity in order to better encapsulate the drug and stabilize the formed particulate. In certain aspects, most of the folic acid moieties in the formed particulates are located inside the particulates, instead of on the outer surface of the particulates. In yet other aspects, all of the folic acid moieties in the formed particulates are located inside the particulates. In still other aspects, none of the folic acid moieties in the formed particulates) is located on the outer surface of the particulates. In some embodiments, the active agents are not exposed on the surface of the particulate but buried underneath the surface. In some embodiments, the active agents are randomly encapsulated throughout the core portion of the particulate, e.g., the active agents do not segregate inside an inner core of the particulate.

In one aspect, disclosed herein is a formulation based on a polysaccharide-vitamin conjugate for paclitaxel delivery, in the form of a core-shell particulate. In one embodiment, dextran is conjugated with folic acid, and the dextran-folic acid conjugate forms the shell/surface of the particulate. The

TABLE 1

Summary of taxane formulations on the market and clinical trials.

| Drug | Status | Company | Delivery method |
| --- | --- | --- | --- |
| Abraxan ® | On the market, acquired by Celgene Corporation | Abraxis BioScience | Albumin bound PTX |
| ABI-008 | Phase II, Prostate Cancer | Celgene Corporation | Albumin bound Docetaxol |
| Opaxio ® | Phase III, Ovarian cancer | Cell Therapeutics, Inc | Polypeptdie conjugate PTX |
| NK-105 | Phase II, advanced gastric cancer | Nippon KayaKu Co. Ltd | Polyaspartate-PEG Paclitaxel micellar nanoparticle |
| Genexol-PM | Phase II Metastatic Breast Cancer | IGDRASOL | Paclitaxel-loaded micellar diblock copolymer |
| AccurinsTM | Phase I, solid tumor | BIND Biosciences, Inc | Polymer trapping Docetaxel |

None of the formulations in Table 1 uses polysaccharides as the vehicle to deliver taxanes. In U.S. Patent Application Publication No. 2007/0213393, hyaluronic acid is used as a polysaccharide hydrogel to entrap paclitaxel dispersed in microemulation formulated by lipid or PLGA. Polymeric paclitaxel particulates (e.g., nanoparticles) can be prepared by methods known in the art, such as the interfacial deposition method as described by Fessi et al., Int. J. Pharm. 1989, and specifically for the preparation of paclitaxel-PLGA nanoparticles by Fonseca et al., J. Control. Rel. 2002.

In Japanese Patent Application JP2010126533A, dextran is chemically linked with paclitaxel to increase the solubility of paclitaxel. Folic acid (FA) is physically absorbed on the surface of the conjugate to increase the target effect of anti-cancer therapy. However, experiments have shown that the chemically conjugated paclitaxel is not active until it is released from the backbone. Moreover, racemization is difficult to be avoided during the drug modification reactions. Another disadvantage is that the targeting ligand folic acid is easy to elute since the physical absorption is not strong to retain the ligand.

In one aspect, disclosed herein is a formulation based on a polysaccharide-vitamin conjugate for paclitaxel delivery, hydrophobic drug, paclitaxel, is entrapped in the particle. In certain aspects, the vitamin (e.g., folic acid) and/or the polysaccharide can be modified to increase the hydrophobicity in order to better entrap the drug and stabilize the formed nanoparticles. In certain aspects, most of the folic acid moieties in the formed core-shell nanoparticles are located inside the nanoparticles, between the drug and the dextran moieties, instead of on the outer surface of the nanoparticles. In yet other aspects, all of the folic acid moieties in the formed core-shell nanoparticles are located inside the nanoparticles, between the drug and the dextran moieties.

In certain aspects, preparation of the particulates (e.g., microparticles) and compositions disclosed herein does not involve chemical modification of the drug, including chemical reactions that would lead to racemization. In preferred embodiments, complex purification procedures for the formulation can be avoided. In preferred embodiments, manufacture cost can be reduced significantly since there are no biological materials such as human proteins involved in the formulation process.

In certain embodiments, in addition to a particulate encapsulating a therapeutic agent, a composition of the present disclosure can further comprise at least one of the following: a co-solvent solution, liposomes, micelles, liquid crystals, nanocrystals, emulsions, microspheres, nanospheres, nanocapsules, polymers or polymeric carriers, surfactants, suspending agents, complexing agents such as cyclodextrins or adsorbing molecules such as albumin (e.g., BSA), surface active particles, and chelating agents.

1. Vitamins and Related Agents

In certain aspects of the present disclosure, molecules essential for cell growth, for example, vitamins and related agents, can be used in the preparation of the particulates (e.g., microparticles) and compositions. A listing of vitamins and related agents that can be included in the particulates (e.g., microparticles) and compositions of the present disclosure may be found in established reference guides, such as the United States Pharmacopeia National Formulary Official Compendium of Standards (i.e., the U.S.P.-N.F. Official Compendium of Standards) or European Directive 90/496/EEC including amendments, which are incorporated herein by reference.

Vitamins and related entities, for example, vitamin analogues, vitamin derivatives and modified vitamins, which can be included in the particulates (e.g., microparticles) and compositions of the present disclosure include but are not limited to Vitamin A (and Vitamin A precursors), thiamin (Vitamin B1), riboflavin (Vitamin B2), niacin (Vitamin B3), pyridoxine (Vitamin B6), folic acid, cobalamins (Vitamin B12), Pantothenic acid (Vitamin B5), Vitamin C, Vitamin D, Vitamin E, Biotin, Vitamin K, other B complex vitamins, B complex related compounds such as Choline and Inositol, for example, and carotinoids such as lutein, lycopene, zeaxanthin, and astaxanthin.

It will be understood that derivatives and analogues of vitamins are within the scope of the present disclosure. Analogues contemplated herein include, but are not limited to, modification to the ring structure, functional groups or side chains of the vitamin molecule including the additional removal of protecting groups and salts and complexes thereof derived from any source such as being chemically synthesized or identified by screening process such as natural product screening provided that the analogue possesses some binding activity for the vitamin receptor. It will be understood by those skilled in the art that upregulated receptors other than just the vitamin receptors on tumor or cancer cells can be targeted.

Folic acid (also known as folate, vitamin M, vitamin B9, vitamin Bc (or folacin), pteroyl-L-glutamic acid, pteroyl-L-glutamate, and pteroylmonoglutamic acid) are forms of the water soluble vitamin B9. Folate is composed of the aromatic pteridine ring linked to para-aminobenzoic acid and one or more glutamate residues. Folic acid is itself not biologically active, but its biological importance is due to tetrahydrofolate and other derivatives after its conversion to dihydrofolic acid in the liver. Folic acid and folate are essential for numerous bodily functions. Humans cannot synthesize folic acid de novo; therefore, folic acid has to be supplied through the diet to meet their daily requirements. The human body needs folic acid to synthesize DNA, repair DNA, and methylate DNA as well as to act as a cofactor in certain biological reactions. It is especially important in aiding rapid cell division and growth, such as in infancy and pregnancy. Children and adults both require folic acid to produce healthy red blood cells and prevent anemia.

Folic acid enters cells either through a carrier protein, termed the reduced folate carrier, or via receptor-mediated endocytosis facilitated by the folate receptor. There are two folate receptors FR-$\alpha$, and FR-$\beta$. The folate receptor FR-$\alpha$ is a 38 KD GPI-anchored protein that binds folic acid with high affinity (<1 nM). Following receptor binding, rapid endocytosis delivers the vitamin into the cell, where it is unloaded in an endosomal compartment at low pH. Importantly, covalent conjugation of small molecules, proteins, and even liposomes to folic acid does not block the vitamin's ability to bind the folate receptor, and therefore, folate-drug conjugates can readily be delivered to and can enter cells by receptor-mediated endocytosis.

Because most cells use an unrelated reduced folate carrier to acquire the necessary folic acid, expression of the folate receptor is restricted to a few cell types. With the exception of kidney, choroid plexus, and placenta, normal tissues express low or nondetectable levels of the folate receptor. It has been reported that FR-$\beta$, the nonepithelial isoform of the folate receptor, is expressed on activated (but not resting) synovial macrophages. Thus, folate receptors are expressed on a subset of macrophages (i.e., activated macrophages). FR$\beta$ is also found on activated monocytes. Accordingly, the present disclosure also relates to using the microparticle or composition disclosed herein, such as a polysaccharide-folic acid conjugate based microparticle, for treatment of inflammation or diseases and conditions that have an inflammation component.

The folate receptor is significantly over-expressed on a large fraction of human cancer cells including ovarian, breast, lung, endometrial, renal, colon, and cancers of myeloid hematopoietic cells. In general FR-$\alpha$, is upregulated in malignant tissues of epithelial origin such as ovarian carcinoma, while FR-$\beta$ is overexpressed in malignant tissues of nonepithelial origin. While the FR have been detected in normal tissues involved in the retention and uptake of the vitamin, these tissues are in protected sites and generally not accessible following blood-borne delivery of folate conjugates. There is expression in the choroid plexus, the intestinal brush border apical membrane surface and the proximal tubules of the kidney. In the latter case the receptor probably functions to scavenge excreted folate, and as such would not be accessible to large molecule weight folate complexes.

In certain aspects of the present disclosure, the particulates and compositions based on the polysaccharide-vitamin conjugates, for example, folic acid-based therapeutic formulations, can be used for delivery of low-molecular-weight chemotherapeutic agents, therapeutic antibodies, protein toxins, radio-imaging agents, radiotherapeutic agents, MRI contrast agents, liposomes with entrapped drugs, genes, antisense oligonucleotides, ribozymes, and immunotherapeutic agents. In particular, particulates based on the polysaccharide-vitamin conjugates (including the dextran-folic acid conjugates) can be used to deliver to a cell, for example, a cancer cell, therapeutic or diagnostic agents listed above. In preferred embodiments, the particulates based on the polysaccharide-vitamin conjugates have a substantially hydrophilic surface, and the active agent (e.g., therapeutic or diagnostic agents) are encapsulated in a core portion of the particulates. In some embodiments, the active agents are not exposed on the surface of the particulate but buried underneath the surface. In some embodiments, the active agents are randomly encapsulated throughout the core portion of the particulate, e.g., the active agents do not segregate inside an inner core of the particulate.

In certain aspects of the present disclosure, the particulates (e.g., microparticles) and compositions based on the polysaccharide-vitamin conjugates, for example, folic acid-based therapeutic formulations, can be used for delivery of low-molecular-weight chemotherapeutic agents, therapeutic antibodies, protein toxins, radio-imaging agents, radiotherapeutic agents, MRI contrast agents, liposomes with entrapped drugs, genes, antisense oligonucleotides, ribozymes, and immunotherapeutic agents. In particular, particulates (e.g., microparticles) based on the polysaccharide-vitamin conjugates (including the dextran-folic acid conjugates) can be used to deliver to a cell, for example, a cancer cell, therapeutic or diagnostic agents listed above. In preferred embodiments, the particulates (e.g., microparticles) based on the polysaccharide-vitamin conjugates have a shell-core structure, and the shell comprises the polysaccharide-vitamin conjugate, and the core comprises the therapeutic or diagnostic agents listed above entrapped in the shell. In certain aspects, the polysaccharide-vitamin conjugate comprises molecules of a vitamin or derivative thereof covalently linked to a polysaccharide, and the molecules of the vitamin or derivative thereof are located between the core and the polysaccharide.

In any of the embodiments disclosed herein, the vitamin can be folate, nicotinamide, N,N-diethylnicotinamide, biotin, sodium salicylate, or any combination thereof. For example, polysaccharide-folate conjugates and polysaccharide-nicotinamide conjugates can be mixed to form the particulate of the present disclosure. In certain embodiments, one or more hydrophobic or fat-soluble vitamins and/or related agents can be used in the particulates (e.g., microparticles).

Vitamins can also be modified according to the present disclosure. For example, folic acid can be modified by amination, e.g., by the reaction shown in FIG. 1C. In certain aspects, vitamins and polysaccharides can be modified to increase the hydrophobicity in order to better entrap the drug and stabilize the formed particulates (e.g., nanoparticles).

2. Polymers Including Polysaccharides

In certain embodiments, a polysaccharide of the present disclosure can comprise hyaluronic acid and derivatives thereof. In preferred embodiments, a polysaccharide of the present disclosure can comprise dextran and derivatives thereof. In certain embodiments, the polysaccharide can be a cyclodextrin or a cyclic oligosaccharide.

In yet other embodiments, a polysaccharide of the present disclosure can comprise cellulose and derivatives thereof (e.g., methylcellulose, hydroxy-propylcellulose, hydroxypropylmethylcellulose, carboxymethylcellulose, cellulose acetate phthalate, cellulose acetate succinate, cellulose acetate butyrate, hydroxypropylmethyl-cellulose phthalate), chitosan and derivative thereof, β-glucan, arabinoxylans, carrageenans, pectin, glycogen, fucoidan, chondrotin, pentosan, keratan, alginate, or cyclodextrins, or salts and derivatives, including esters and sulfates, thereof. A combination of two or more of the polysaccharides disclosed herein may be admixed, to form conjugates with one or more types of vitamins or related agents, to form the particulates (e.g., microparticles) of the present disclosure. In addition, co-polymers formed between monomers of two or more of the polysaccharides disclosed herein are also contemplated for use in the preparation of the particulates (e.g., microparticles) and compositions of the present disclosure.

In some embodiments, the polysaccharide of the present disclosure is a polysaccharide soluble in an organic solvent. By having a polysaccharide soluble in the organic solvent, the conjugation reaction with the vitamin can be efficiently conducted. Examples of suitable organic solvent include dimethylsulfoxide, N,N-dimethylformamide, tetrahydrofuran (THF), dioxane, oxalic acid, and the like. Optionally, the polysaccharide is a polysaccharide having exclusively carbon, oxygen, and hydrogen atoms. Optionally, the polysaccharide is a dextran or derivative thereof.

In certain aspects, large molecular weight polymer complexes can be used to conjugate vitamins or related agents to form polymer-vitamin conjugates, for use in the particulates (e.g., microparticles) and/or composition of the present disclosure. For example, polysaccharide-vitamin conjugates can form the particulates entrapping the agent or active substance to be delivered. In preferred embodiments, the particulates based on the polysaccharide-vitamin conjugates have a substantially hydrophilic surface, and the active agent (e.g., therapeutic or diagnostic agents) are encapsulated in a core portion of the particulates. In some embodiments, the active agents are not exposed on the surface of the particulate but buried underneath the surface. In some embodiments, the active agents are randomly encapsulated throughout the core portion of the particulate, e.g., the active agents do not segregate inside an inner core of the particulate. Optionally, polysaccharide-vitamin conjugates can form the shell of the microparticle, entrapping the agent or active substance to be delivered. In some embodiments, a biocompatible polymer backbone to which a number of vitamin molecules are linked forms the shell, and a drug forms the core but is not covalently linked to the polymer backbone or the vitamin moiety. Such an arrangement can enhance the efficiency of drug delivery and preserve the biological activity of the drug.

In certain other aspects, the particulates (e.g., microparticles) can comprise polymers other than polysaccharides. For example, PCT/AU00/00406 discloses a folate-polymer complex and uses thereof, and U.S. Pat. No. 5,449,720 discloses a VB12-polymer complex and uses thereof, both specifications of which are incorporated herein in their entirety by reference. Vitamin-coated particulates (e.g., nanoparticles) are also disclosed in PCT/AU00/00405, and in EP 0,531,497 B1, both specifications of which are incorporated herein in their entirety by reference. Polymers suitable for the formation of particulates (e.g., microparticles and nanoparticles), include, amongst others, polylactic acid, poly-(Lactide/co-glycolide), poly-hydroxybutyrate, poly-hydroxyvalerate, poly-(hydroxybutyrate/valerate), ethyl cellulose, dextran, polysaccharides, poly-alkylcyanoacrylate, poly-methyl-methacrylate, poly(e-caprolactone) and various combinations and co-polymers thereof. In certain aspects, particulates (e.g., nanoparticles) are formed from the polymers with conjugated vitamin moieties by solvent evaporation or in-liquid drying.

In certain other aspects, particulates (e.g., microparticles) or microspheres can be formed from the polymers with conjugated vitamin moieties by interfacial precipitation/polymerization. In certain aspects, the polymers include, amongst others, polymers formed by the reaction of lysine hydrochloride and p-phthaloyl dichloride, or by the reaction of acryloylated maltodextrin or acryloylated hydroxyethyl starch with ammonium peroxodisulfate and N,N,N',N'-tetramethylethylenediamine. Polymers suitable for the formation of particulates (e.g., microparticles) or microspheres by polymer phase separation include co-poly(vinyl chloride: vinyl alcohol: vinyl acetate), cellulosic polymers, polyvinyl acetate, polyvinyl alcohol, polyvinylchloride, natural and synthetic rubbers, polyacrylates, polystyrene and the like. Methods to synthesize such particulates (e.g., microparticles) s or microspheres are fully described in U.S. Pat. No. 4,166,800, the disclosure of which is incorporated by reference for all purposes. Other polymers suitable for the formation of particulates (e.g., microparticles) s or microspheres include, amongst others, mixtures of polyanions, such as gum arabic, alginate, carboxymethyl cellulose, carboxymethyl starch, polystyrene sulfonic acid, polyvinyl sulfonic acid, poly-d-glucuronic acid, poly-pyruvic acid, carrageenan, heparin sulphate, polyphosphate with polycations, such as polylysine, gelatin, cross-linked gelatin, starch, cross-linked albumen, polyacrylamide, and others known to those skilled in the art of particulates (e.g., microparticles) and/or microsphere preparation. Without being bound by any theory, a polypeptide comprising homopolymers of polyamino acids such as poly(L-glutamic acid), polypeptides, proteins, peptides, co-polymers of polyamino acids, collagen, albumin, fibrin, or gelatin, may also be included in the particulates (e.g., microparticles) s, for example, as a component. Polymers useful according to the present disclosure include potentially biodegradable polymers such as dextran and its derivatives, and amino acid polymers such as poly-lysine and poly-glutamic acid. In certain embodiments, an advantage of using polymers (such as polysaccharides) in combination with folic acid and a therapeutic agent is that targeting to the kidneys can be avoided or reduced due to of the size of the polymers.

In one embodiment, the linkage joining the vitamin or related molecule to the polymer can comprise a disulfide bond, an ester linkage, a γ-glutamyl-ε-lysine bond, and/or a diazo-linkage. In preferred embodiments, the therapeutic agent to be delivered to a cancer cell in the particulates (e.g., microparticles) is itself not covalently bound or conjugated to the polymer. Nonetheless, polymers such as polysaccharides can be linked, either covalently or non-covalently, to various enzymes, drugs, and cytotoxic agents for the control of tumor cell growth, for example, by way of combination therapy.

3. Active Agents

In preferred embodiments, particulates (e.g., microparticles) of the present disclosure entrap and/or deliver therapeutic and/or diagnostic agents or other active substances to a subject in need thereof. The agents or active substances can include, hormones, drugs, prodrugs, enzymes, proteins, peptides, toxins, immunogens, DNA and analogues, and RNA and analogues. For example, suitable agents for use in the present disclosure include, but are not limited to, ricin, abrin, diphtheria toxin, modecin, tetanus toxin, mycotoxins, melittin, α-amanitin, pokeweed antiviral protein, ribosome inhibiting proteins, especially those of wheat, barley, corn, rye, gelonin, maytansinoid.

The therapeutic agents or active substances can also include cytotoxic agents, such as alkylating agents (e.g., chlorambucil, cyclophosphamide, melphalan, cyclopropane), anthracycline antitumor antibiotics (e.g., doxorubicin, daunomycin, adriamycin, mitomycin C, 2-(hydroxymethyl)anthraquinone), antimetabolites (e.g., methotrexate, dichloromethatrexate), cisplatin, carboplatin, and metallopeptides containing platinum, copper, vanadium, iron, cobalt, gold, cadmium, zinc and nickel. Other agents include deoxynivalenol, thymidine, pentamethylmelamin, dianhydrogalactitol, 5-Methyl-THF, anguidine, maytansine, neocarzinostatin, chlorozotocin, AZQ, 2'-deoxycoformycin, PALA, valrubicin, m-AMSA and misonidazole.

In preferred embodiments, the therapeutic agents can be hydrophobic drugs, i.e., water insoluble drugs or poorly water-soluble drugs. The term "hydrophobic drug" may refer to a drug, usually a therapeutic drug, that exhibits a characteristic of absorption by a lipophilic moiety, for example, a lipoprotein, or of reduced solubility in a polar medium. Hydrophobic drugs can include, but are not limited to, glucocorticoids, cytostatics, certain antibodies, drugs acting on immunophilins, interferons, opiates, INF binding proteins, mycophenolate, FTY720, cyclosporin (including cyclosporin A, cyclosporin B, cyclosporin C, cyclosporin D, cyclosporin E, cyclosporin F, cyclosporin G, cyclosporin H, cyclosporin I), tacrolimus (FK506, PROGRAF®), sirolimus (rapamycin, RAPAMUNE®), everolimus (RAD, CERTICAN®), taxanes such as paclitaxel, discodermolide, colchicine, vinca alkaloids such as vinblastine or vincristine, and analogues or derivatives of any of the listed agents.

In preferred embodiments, the poorly water-soluble drug is a taxane compound or analogue thereof. Examples of taxane compounds include paclitaxel, docetaxel, 7-epi paclitaxel, t-acetyl paclitaxel, 10-desacetyl-paclitaxel, 10-desacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, cabazitaxel or a mixture thereof.

In preferred embodiments, the poorly water-soluble drug is a camptothecin compound. Examples of camptothecin compounds include irinotecan (CAMPTOSAR; 7-ethyl-10-[4-(1-piperidino)-1-piperidino]-carbonyloxycamptothecin), topotecan (HYCAMPTIN; (S)-9-N;N-dimethylaminoethyl-10-hydroxycamptothecin), 9-aminocamptothecin (9-amino-20(S)-camptothecin), 9-nitrocamptothecin (also called rubitecan), lurtotecan (7-(4-methylpiperazinomethylene)-10,11-ethylenedioxy-20(S)-camptothecin), exatecan, karenitecin, and a homocamptothecin. The structures and clinical information for some camptothecin compounds can be found in Garcia-Carbonero, et al., Clin. Cancer Res. (March 2002) 8: 641-661. Examples of camptothecin compounds can also be found in U.S. Pat. Nos. 4,604,463, 6,403,569, and 5,004,758, and in WO2004/012661, WO2003/101998, WO2003/101996, WO2003/101406, WO2003/093274, WO2003/086471, WO01/76597, WO01/64194, WO00/70275, WO00/53607, WO99/17805, WO99/17804, WO99/05103, WO98/35969, WO97/28164, WO97/25332, WO97/16454, the contents of all of which are incorporated herein by reference in its entirety.

In preferred embodiments, the therapeutic agent is paclitaxel, a compound that disrupts mitosis (M-phase) by binding to tubulin to form abnormal mitotic spindles, or an analogue or derivative thereof. Paclitaxel is a highly derivatized diterpenoid (Wani et al., *J. Am. Chem. Soc.* 93:2325, 1971). "Paclitaxel" (which should be understood herein to include formulations, prodrugs, epimers, isomers, analogues and derivatives such as, for example, TAXOL®, TAXOTERE®, docetaxel, 10-deacetyl analogues of paclitaxel, etc.) may be readily prepared utilizing techniques known to those skilled in the art (e.g., Schiff et al., *Nature* 277:665-667, 1979; Long and Fairchild, *Cancer Research* 54:4355-4361, 1994; Ringel and Horwitz, *J Nat'l Cancer Inst.* 83(4):288-291, 1991; Pazdur et al., *Cancer Treat. Rev.* 19(4):351-386, 1993; WO 94/07882; WO 94/07881; WO 94/07880; WO 94/07876; WO 93/23555; WO 93/10076; WO94/00156; WO 93/24476; EP 590267; WO 94/20089; U.S. Pat. Nos. 5,294,637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,248,796; 5,422,364; 5,300,638; 5,294,637; 5,362,831; 5,440,056; 4,814,470; 5,278,324; 5,352,805; 5,411,984; 5,059,699; 4,942,184; *Tetrahedron Letters* 35(52):9709-9712, 1994; *J. Med Chem.* 35:4230-4237, 1992; *J. Med Chem.* 34:992-998, 1991; *J. Natural Prod.* 57(10):1404-1410, 1994; *J. Natural Prod.* 57(11):1580-1583, 1994; *J. Am. Chem. Soc.* 110:6558-6560, 1988), the contents of all of which are incorporated herein by reference in its entirety; or obtained from a variety of commercial sources, including for example, Sigma, St. Louis, Mo.

4. Polysaccharide-Vitamin-Active Agent Combinations

In certain embodiments, different vitamins can be conjugated to the same type of polysaccharide, or the same vitamin can be conjugated to different types of polysaccharides. In other embodiments, conjugates with different combinations of the vitamin and polysaccharide moieties can be mixed and used in the preparation of the particulates (e.g., microparticles) s. In certain embodiments, conjugates containing different vitamin moieties are used in conjunction with the same therapeutic agent. Administration of the particulates (e.g., microparticles) s or compositions so produced can result in the particulates (e.g., microparticles) s targeting cancer cells which exhibit upregulated expression and/or activity of the vitamin receptors, while at the same time unwanted accumulation of the particulates (e.g., microparticles) s is spread over different organs and tissues which also happen to be targeted by the particular vitamins. In this case, delivery of the therapeutic agent to the target cells can be enhanced without increasing toxicity of the therapeutic agent to other parts of the body. In another embodiment, conjugates containing the same vitamin moiety can be used in conjunction with different therapeutic agents, therefore enabling combinatorial therapy. For example, different agents may be targeted to the same cancer cell populations for enhanced and/or synergistic killing.

In preferred embodiments, the specific polysaccharide-vitamin-therapeutic agent combination can be determined based on the tissue origin and/or gene expression profiles of the cancer to be treated using the particulate (e.g., a microparticle) or composition of the present disclosure. The types of cancer that could benefit from the present disclosure include, but are not limited to, chronic leukemia, breast cancer, sarcoma, ovarian carcinoma, rectal cancer, throat cancer, melanoma, colon cancer, bladder cancer, lung cancer, mammary adenocarcinoma, gastrointestinal cancer, stomach cancer, prostate cancer, pancreatic cancer, or Kaposi's sarcoma. Other cancers not articulated herein but well known to those skilled in the art are also considered to be envisaged within the scope of this disclosure. Information on a subject's responsiveness to certain therapies can also be considered when choosing the polysaccharide-vitamin-therapeutic agent combination.

5. Linker Molecules and Linker Groups

In some embodiments, the polysaccharide is conjugated to each of the one or more molecules of a vitamin or analogue or derivative thereof through a linker molecule comprising a first chemical group reactive to one or more functional groups on the polysaccharide, and a second chemical group reactive to one or more functional groups on each of the one or more molecules of a vitamin or analogue or derivative thereof. It was discovered in the present disclosure that the efficacy of a drug delivered by the polysaccharide-vitamin conjugate is much enhanced by having a linker molecule, as compared to that of the drug delivered by a polysaccharide-vitamin conjugate which is directly conjugated without a linker molecule. As used herein, the functional group may refer to an inherent function group of a molecule (e.g., the polysaccharide, the vitamin or analogue or derivative thereof), or a functional group added via bonding to the molecule as a result of functionalization. For example, the polysaccharide may be functionalized using succinic acid to obtain a carboxylic acid functional group, which is capable of reacting with a linker molecule having an amine chemical group to form an amide bond.

Optionally, the linker molecule includes the first chemical group and the second chemical group without a spacer in-between. Optionally, the linker molecule includes the first chemical group, the second chemical group, and a spacer between the first chemical group and the second chemical group.

In some embodiments, the linker molecule includes the first chemical group, the second chemical group, and the spacer between the first chemical group and the second chemical group. Optionally, the spacer includes 1 to 50 atoms. Optionally, the spacer includes 1 to 50 carbon atoms, e.g., 1 to 15 carbon atoms, 1 to 20 carbon atoms, 20 to 35 carbon atoms, or 35 to 50 carbon atoms.

In some embodiments, the linker molecule is an organic molecule having two functional groups. Examples of organic molecules having two functional groups include, but are not limited to, a diamine, a dicarboxylic acid, and the like. Optionally, the organic molecule having two functional groups has a linear chain with 2 to 20 carbon atoms, e.g., 2 to 6 carbon atoms, 6 to 10 carbon atoms, or 10 to 20 carbon atoms.

Examples of diamine linker molecules include, but are not limited to, methylenediamine, ethylene diamine, 1,2-diaminopropane, 1,3-propanediamine, N-methyl-1,3-diaminopropane, N,N'-dimethyl-1,3-propanediamine, 2,2-dimethyl-1,3-propanediamine, 1,3-diamino-2-propanol, 1,4-diaminobutane, 1,5-diaminopentane, 1,6-diaminohexane, 1,7-diaminoheptane, and 1,8-diaminooctane. Examples of dicarboxylic acid linker molecules include, but are not limited to, ethanedioic acid, propanedioic acid, butanedioic acid, malic acid, tartaric acid, fumaric acid, pentanedioic acid, hexanedioic acid, heptanedioic acid, octanedioic acid, nonanedioic acid, decanedioic acid, 1,11-undecanedicarboxylic acid, 1,12-dodecanedicarboxyliic acid, and hexadecanedioic acid.

In some embodiments, the linker molecule is a polymer having the first chemical group at, or near to, a first terminus of the polymer chain, and a second chemical group at, or near to, a second terminus of the polymer chain; the first terminus contralateral to the second terminus. Examples of polymer suitable for making the linker molecule includes, but are not limited to, polyethylene glycol, poly-amino acid, poly-lactic acid, poly(lactic-co-glycolic acid), and the like.

In some embodiments, the polysaccharide may be functionalized prior to reacting with the linker molecule. Optionally, the polysaccharide is functionalized with a succinic acid. In some embodiments, the vitamin or analogue or derivative thereof may be functionalized prior to reacting with the linker molecule.

Accordingly, in some embodiments, the polysaccharide-vitamin conjugate includes a linker group covalently linking the polysaccharide and each of the one or more molecules of a vitamin or analogue or derivative thereof. The linker group is the reaction product among the linker molecule, the polysaccharide, and the vitamin or analogue or derivative thereof. For example, the first chemical group of the linker molecule reacts with a functional group of the polysaccharide, forming a first covalent bond linking the linker molecule and the polysaccharide; the second chemical group of the linker molecule reacts with a function group of the vitamin or analogue or derivative thereof, forming a second covalent bond linking the linker molecule and the vitamin or analogue or derivative thereof. Examples of first covalent bond and second covalent bond include an amide bond, an ester bond, a disulfide bond, a γ-glutamyl-ε-lysine bond, and a diazo linkage.

In some embodiments, the linker group includes a spacer between the first covalent bond and the second covalent bond. Optionally, the spacer includes 1 to 50 atoms. Optionally, the spacer includes 1 to 50 carbon atoms, e.g., 1 to 15 carbon atoms, 1 to 20 carbon atoms, 20 to 35 carbon atoms, or 35 to 50 carbon atoms.

In some embodiments, one or both of the first covalent bond and the second covalent bond is a biodegradable linkage. Examples of biodegradable linkages include an amide bond, which can be cleaved by enzymes in blood such as aminopeptidase and pepsin. It was discovered in the present disclosure that a polysaccharide-vitamin conjugate having an amide bond as the first covalent bond and/or the second covalent bond undergoes spontaneous degradation in blood even under a mild condition.

6. Conjugation Sites and Types

The polysaccharide-vitamin conjugate of the present disclosure may have any appropriate number of conjugation sites. In some embodiments, the polysaccharide-vitamin conjugate has an average number of conjugation sites in a range of 1 to 10, e.g., 1 to 5, 1 to 4, 1 to 3, or 1 to 2. Optionally, the polysaccharide-vitamin conjugate has an average number of conjugation sites of 1. Optionally, the polysaccharide-vitamin conjugate has an average number of conjugation sites of 2. The average number of conjugation sites may be controlled by, e.g., a ratio between the polysaccharide and the vitamin in the conjugation reaction.

In some embodiments, the polysaccharide-vitamin conjugate includes a single type of vitamin or analogue or derivative thereof. In some embodiments, the polysaccharide-vitamin conjugate includes a plurality of types of vitamin or analogue or derivative thereof in each conjugate molecule. Optionally, the polysaccharide-vitamin conjugate includes 2 to 10 (e.g., 2 to 5, 2 to 4, 2, 4, or 5) different types of vitamins or derivatives thereof in each conjugate molecule. Optionally, each conjugate molecule may include 2 to 5 different types of vitamins or derivatives thereof (e.g., folic acid, cholic acid, vitamin A, vitamin E, or derivatives thereof).

In some embodiments, the particulate is formed by a polysaccharide-vitamin conjugate including a single type of vitamin or analogue or derivative thereof. In some embodiments, the particulate is formed by a polysaccharide-vitamin conjugate including a plurality of types of vitamin or analogue or derivative thereof in each conjugate molecule. In some embodiments, the particulate is formed by a mixture of polysaccharide-vitamin conjugates, some of which includes a single type of vitamin or analogue or derivative thereof in each conjugate molecule, and some of which includes a plurality of types of vitamin or analogue or derivative thereof in each conjugate molecule.

Preparation of Particulates Encapsulating Active Agents

Figure 2:
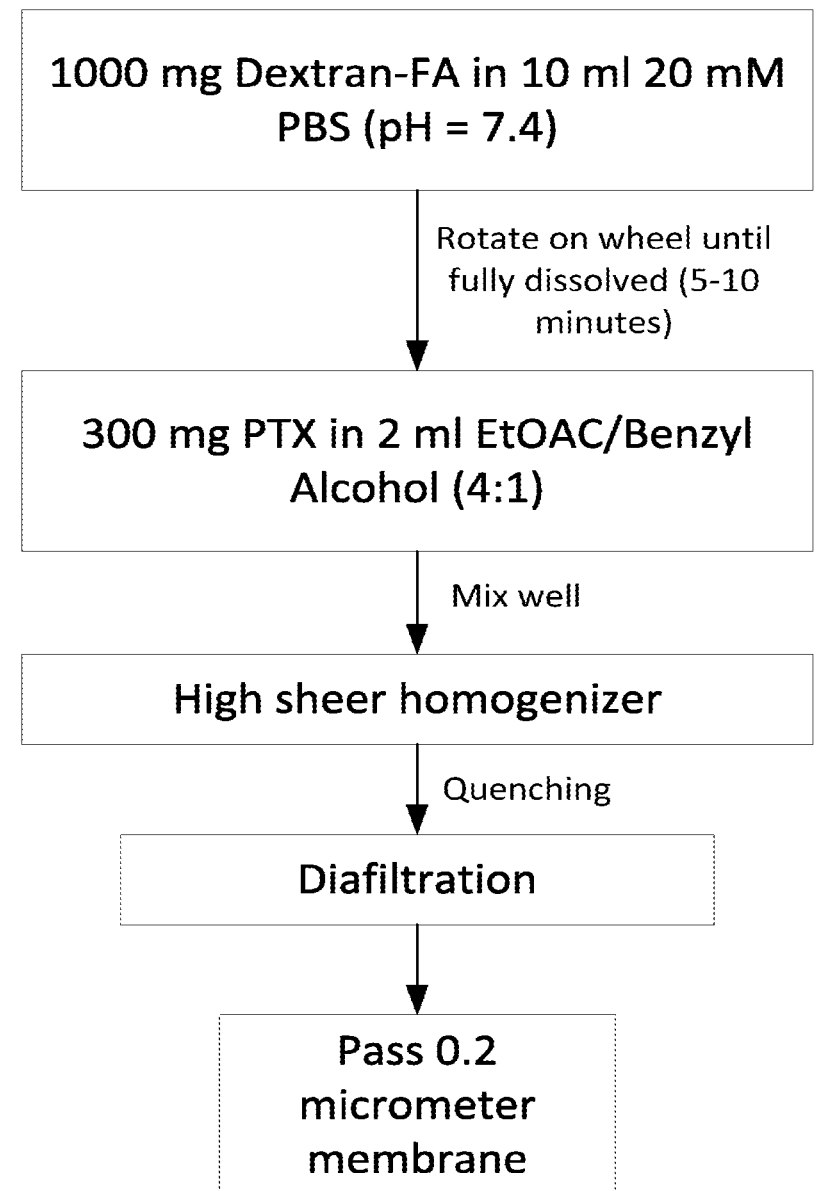
FIG. 2 is a flow chart illustrating an encapsulation process for preparing a formulation comprising a microparticle, according to some embodiments of the present disclosure.

A process for preparing a composition comprising the particulate (e.g., a microparticle) of the present disclosure is provided, for example, in FIG. 2. In one aspect, the process comprises: providing a polysaccharide-vitamin conjugate comprising one or more molecules of a vitamin or analogue or derivative thereof covalently linked to a polysaccharide; combining the polysaccharide-vitamin conjugate and the therapeutic agent in a suitable solvent, or combining a solution of the polysaccharide-vitamin conjugate and a solution of the therapeutic agent; and subjecting the mixture of the polysaccharide-vitamin conjugate and the therapeutic agent to a high sheer homogenizer to form a composition comprising a particulate (e.g., a microparticle) comprising the polysaccharide-vitamin conjugate and the therapeutic agent, wherein the therapeutic agent is entrapped in a particulate formed by the polysaccharide-vitamin conjugate and the one or more molecules of a vitamin or analogue or derivative thereof are located between the therapeutic agent and the polysaccharide.

In one embodiment, a dextran-folic acid conjugate can be prepared as follows. Dextran has both 1,3-linkage and 1,6 linkage. As a result, there are different hydroxyl groups available for the first step derivatization. Synthesis of succinylated dextran (MW=10-70 KDa) is shown below and in FIG. 1A (1, 6 dextran) and FIG. 1B (1, 3 dextran) to illustrate.

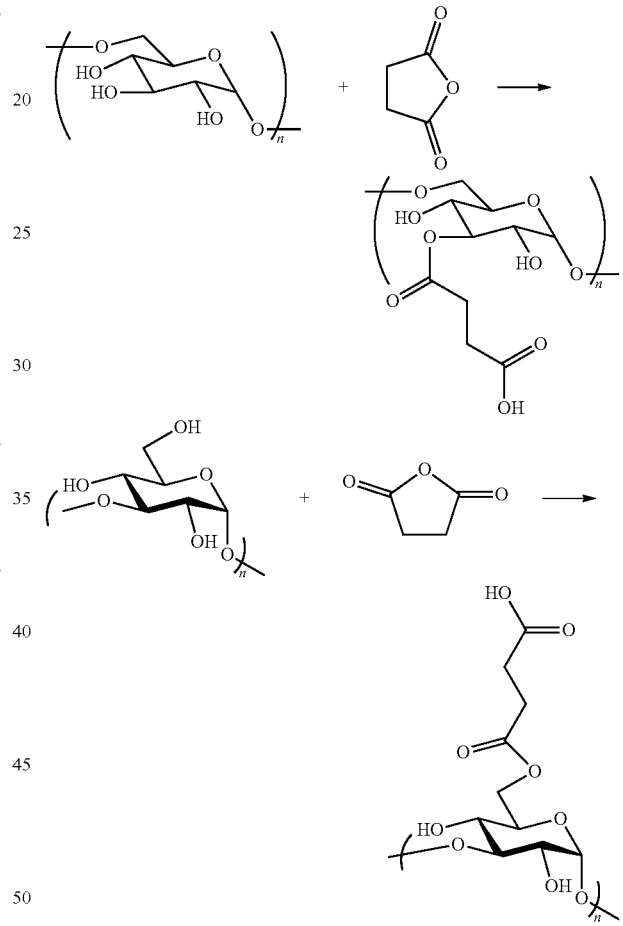

Figure 1B:
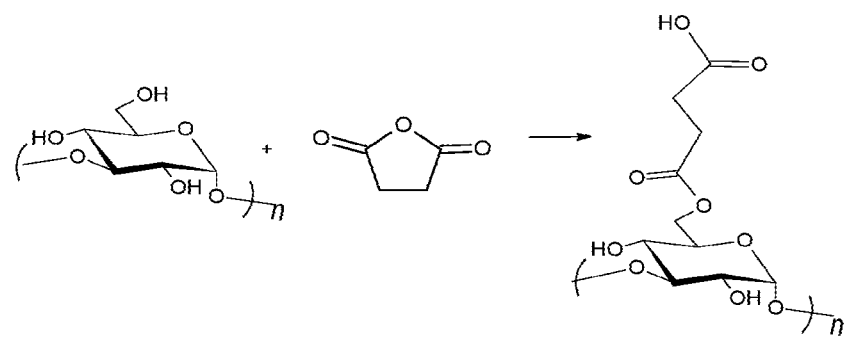
FIG. 1B is a schematic showing the synthesis of succinylated 1, 3 dextran.
Figure 1C:
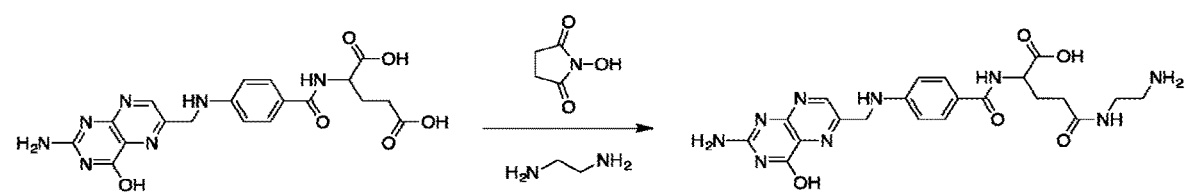
FIG. 1C is a schematic showing the synthesis of amino folic acid.

In one aspect, synthesis of amino folic acid is shown below and in FIG. 1C.

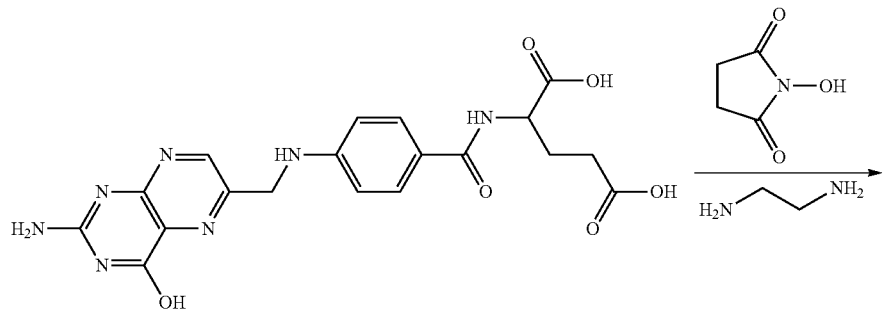

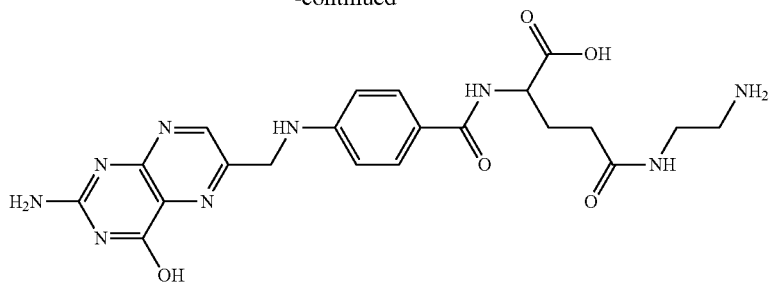

It should be understood that the polysaccharide and the vitamin can be modified separately. Either modification may be carried out before the conjugation step shown below and in FIG. 1D. In certain aspects, either modification or both modifications may be performed concurrently or substantially concurrently with the conjugation step. In other embodiments, modification of the polysaccharide moiety and/or modification of the vitamin (or related agent) moiety can be performed after the moieties are conjugated. In one embodiment, the reaction below links a modified dextran to a modified folic acid to form a dextran-folic acid conjugate. In certain aspects, conjugation to folic acid or derivatives or analogues thereof increases the hydrophobicity of the polysaccharide, for example, dextran. It is to be understood that other vitamins or related agents and other methods to increase the hydrophobicity of the polysaccharide may also be used, either independently or in combination with the methods and processes described herein.

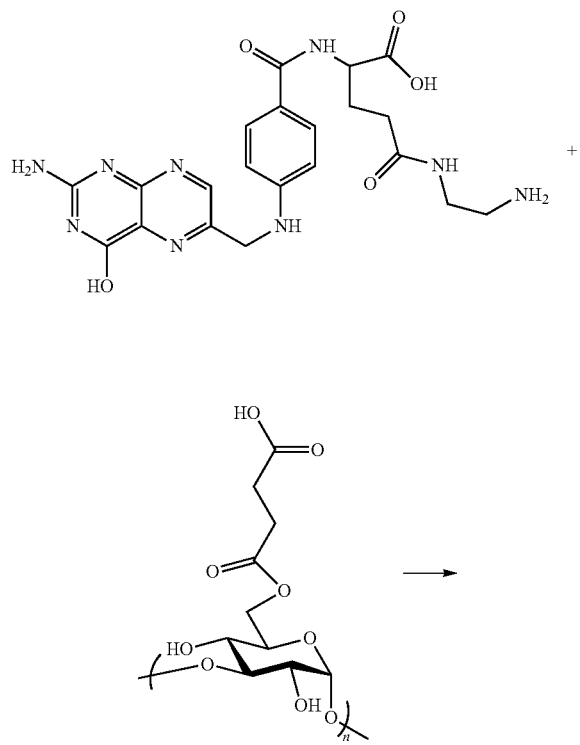

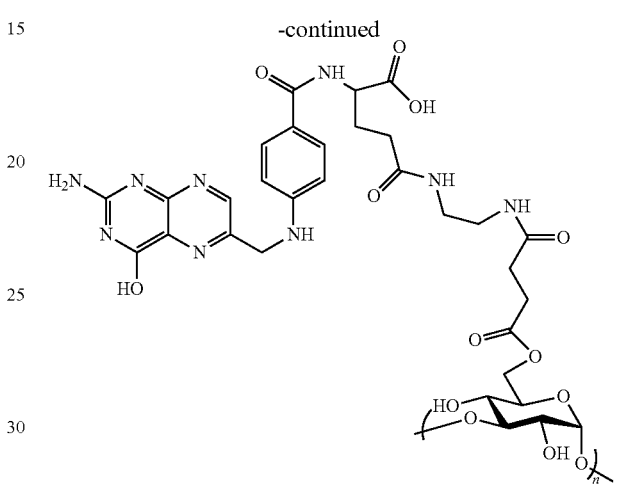

In certain embodiments, the ratio of folic acid to the unit of dextran is (0.5~2):(1.0~20). In preferred embodiments, the ratio of folic acid to the unit of dextran is (0.8~1.2):(2.0~10), and more preferably, 1:5. In certain aspects, carbodiimides such as N,N'-Diisopropylcarbodiimide (DIC) or N,N'-Dicyclohexylcarbodiimide (DCC) can be used as the coupling reagent. As a liquid, DIC is easier for handling than the commonly used DCC.

In one embodiment, a formulation process to entrap a drug into the dextran-folic acid conjugate can be performed as follows, using a high sheer homogenizer to mix an anti-neoplastic agent (e.g., an anti-cancer drug) and the dextran-folic acid conjugate. In preferred embodiments, the anti-neoplastic agent can be paclitaxel, docetaxel, or doxorubicin, or derivatives or analogues thereof, or any combination thereof.

In certain embodiments, the mixing process for a drug and a vehicle can be completed by a normal homogenizer. In preferred embodiments, high-sheer homogenizer is used to entrap a drug into the core of a dextran-folic acid conjugate to form a nano-scale suspension with high encapsulation efficiency. In particular aspects, the mixture of the polysaccharide-vitamin conjugate and the therapeutic agent can be subjected to a high sheer homogenizer under a pressure in the range of about 10,000 to about 30,000 psi (pounds per square inch). In other aspects, a high sheer homogenizer with a pressure in the range of about 5,000 to about 10,000 psi, about 10,000 to about 20,000 psi, about 20,000 to about 30,000 psi, about 30,000 to about 40,000 psi, about 40,000 to about 50,000 psi, about 50,000 to about 60,000 psi, or higher than about 60,000 psi can be used.

In one aspect, a dextran-folic acid conjugate can be dissolved in a suitable buffer, for example, a PBS buffer (pH=7.4). The mixture can be rotated on wheel until the dextran-folic acid conjugate is fully dissolved, typically in about 5-10 minutes. In one embodiment, a drug such as paclitaxel can be dissolved in a suitable buffer or solvent, for example, ethyl acetate/benzyl alcohol (4:1) or $CH_2Cl_2$/ethanol (4:1), and added to the dextran-folic acid conjugate aqueous solution to obtain a crude formulation/emulsion.

In certain embodiments, the solution of the polysaccharide-vitamin conjugate and the solution of the therapeutic agent are miscible. In certain embodiments, the solution of the polysaccharide-vitamin conjugate and the solution of the therapeutic agent are immiscible. For example, the solvent of the polysaccharide-vitamin conjugate is an aqueous liquid (e.g., water or water containing dissolved salts or other species, cell or biological media, ethanol, etc.), and the solvent of the therapeutic agent is an organic solvent (e.g., dichloromethane, acetonitrile, chloroform, tetrahydrofuran, acetone, formamide, dimethylformamide, pyridines, dioxane, dimethysulfoxide, etc.). In some embodiments, combining the solution of the polysaccharide-vitamin conjugate and the solution of the therapeutic agent can result in an emulsion.

In one embodiment, the emulsion can be an oil-in-water type emulsion, the emulsion comprising a dispersed non-aqueous phase containing the particulates (e.g., microparticles), and a continuous phase comprising water. In another embodiment, the non-aqueous phase of the emulsion comprises at least one of benzyl benzoate, tributyrin, triacetin, and an oil such as safflower oil and corn oil. In certain embodiments, the emulsion may be a microemulsion.

In one aspect, a high sheer homogenizer (for example, LM 20, Microfluidics Inc.) can be applied to the crude emulsion at 30,000 psi for about 4 to about 6 times. The whole crude emulsion can be poured into a suitable solvent, for example, cold DI water, under mixing at a ratio of 5:1 (water:emulsion, v/v). In certain embodiments, the process can further comprise isolating the particulate (e.g., a microparticle) by diafiltration, filtration, solvent evaporation, or centrifugation, or any combination thereof. For instance, the solvent in the emulsion can be removed by diafiltration to reach a final concentration of 10 mg/mL polymer. In other embodiments, the process can further comprise isolating the particulate by addition of a co-solvent followed by diafiltration. In certain aspects, the co-solvent can be deionized water.

In certain aspects, the process can further comprise a purifying step and/or a sterilizing step. In certain aspects, the purifying step and/or the sterilizing step can comprise filtering the particulate (e.g., a microparticle) through a membrane of an average pore size of 0.2 μm, and/or washing the particulate with a suitable solvent. For example, the particle size can be measured and a 0.2 μm membrane can be used to sterilize the formulation before lyophilization.

In certain aspects, the process can further comprise a drying step and/or a lyophilization step in the presence of a cryoprotectant, such as a sugar, e.g., sucrose or trehalose. For example, a cyroprotectant, such as about 10 wt % of sucrose can be added to keep the particle size substantially unchanged during the following freezing-dry cycles. In particular embodiments, the lyophilization step does not substantially aggregate the particulate (e.g., a microparticle) or substantially change the average diameter of the particulate. In preferred embodiments, the particulate (e.g., a microparticle) can be a nanoparticle. In certain aspects, an average diameter of the particulate can be between about 20 nm and about 200 nm. In certain other aspects, an average diameter of the particulate can be between about 20 nm and about 50 nm, between about 50 nm and about 100 nm, between about 100 nm and about 150 nm, or between about 150 nm and about 200 nm. In one embodiment, the average diameter of the particulate is less than about 200 nm, and remains less than about 200 nm during and/or after lyophilization.

In preferred embodiments, a long shelf lifetime for the formulation can be achieved by a freezing-dry process. In one aspect, the composition after the lyophilization step can be formulated as a lyo-cake or lyophilized powder. In another aspect, the reconstituted solution demonstrated stability in terms of suspension uniformity and drug content for over 3 days at room temperature.

Within certain embodiments, the particulate (e.g., a microparticle) of the present disclosure can be a nanoparticle, nanosphere, nanocapsule, or micelle containing a therapeutic agent. In preferred embodiments, in the particulates (e.g., microparticles) of the present disclosure, the vitamin or related agent moiety is located between the entrapped drug and modified polysaccharide inside the particulates, instead of on the outer surface of the particle, for example, to function as a target ligand. In addition, in preferred embodiments, a biodegradable polysaccharide is used, and compared to other biomolecules such as albumin, the cost is lower. For example, modification of a polysaccharide and coupling it to other molecules can be achieved more easily and at a lower cost than human albumin. For instance, no gel permeation chromatography (GPC) methods are needed for the polymer purification. In addition, synthetic polymers can reduce the risk of virus contamination of other biological materials such as human albumin, which is used as the vehicle in the benchmark drug on the market.

A further advantage of the present disclosure is that unlike other polymer-drug conjugate delivery system, the drug is physically entrapped into the polymer, and not through chemical or covalent linkage. Therefore, in preferred embodiments, the release rate can be faster than a drug covalently conjugated to the polymer or polymer conjugate. In preferred embodiments, racemization of the drug can be completely avoided, or at least significantly reduced, to retain the drug's potency and/or biological activity.

Formulations

In another aspect, the present disclosure provides a stable formulation having the present particulates. For example, a stable formulation may be prepared by reconstituting a lyophilized particulate in an aqueous solution. The reconstituted sample stays stable for at least 3 days at room temperature, e.g., at least 5 days at room temperature, at least 7 days at room temperature, or at least 10 days at room temperature. The average size of the particulate remains substantially unchanged in the reconstituted sample for at least 3 days at room temperature, e.g., at least 5 days at room temperature, at least 7 days at room temperature, or at least 10 days at room temperature. Moreover, drug loading contents in the particulate remain substantially the same in the reconstituted sample for at least 3 days at room temperature, e.g., at least 5 days at room temperature, at least 7 days at room temperature, or at least 10 days at room temperature.

In another aspect, the present disclosure provides a method of reconstituting a lyophilized particulate prepared by the process described herein. In some embodiments, the reconstitution method includes adding a diluent to the lyophilized particulate to form a reconstituted solution. Optionally, the diluent is sterile, pyrogen-free water. The reconstituted solution is suitable for subcutaneous injection and intravenous injection.

Methods of Using Particulates for Diagnosis, Treatment, and Prognosis

The present disclosure provides a method for treating a subject, comprising administering to the subject an effective amount of the particulate (e.g., a microparticle) or composition of any of the embodiments disclosed herein. In certain aspects, the particulate (e.g., a microparticle) or composition can be configured for administration in a subject via the topical, enteral/gastrointestinal, parenteral, epidural, intracerebral, intracerebroventrical, intradermal, subcutaneous, nasal, oral, intravenous, intraarterial, intramuscular, intraosseous infusion, intravitreal, intravesical, transdermal, or transmucosal route.

It is to be understood that clinical applications of the present disclosure are not limited to cancers or neoplastic diseases or conditions. Rather, any disease or condition may benefit from the use of the particulates (e.g., microparticles) and compositions disclosed herein, provided there are suitable agents that can be entrapped in the particulate, suitable routes for administration, suitable target population of subjects, and suitable methods to monitor a subject's response to the agent(s) to be delivered using the particulate. In particular examples, the diseases or conditions that can benefit from the use of the particulates (e.g., microparticles) and compositions include and are not limited to viral infections, e.g., HIV infection or AIDS, or HBV or HCV infections; autoimmune diseases, e.g., lupus or rheumatoid arthritis; neurodegenerative diseases, e.g., Parkinson's disease or Alzheimer's disease.

In certain embodiments, use of a particulate (e.g., a microparticle) is preferred to entrap and/or deliver an anti-neoplastic agent to a subject in need thereof for diagnostic, therapeutic, and/or prognostic purposes, wherein the anti-neoplastic agent can be selected from the group consisting of alkylating agents, antimetabolites, natural anticancer products, hormones, metal coordination complexes and mixtures thereof. The only requirement is that these agents may be suitably entrapped by the particulates (e.g., microparticles) used in the present disclosure and do not interfere with each other when used in combination. There is no restriction concerning the administration of agents of one single group or of more than one of the above groups which, of course, include numerous substances specifically disclosed herein and below: baccatin III. nitrogen mustards (e.g., Cyclophosphamide, Trofosfamide, Ifosfamide and Chlorambucil), nitrosoureas (e.g., Carmustine (BCNU), Lomustine (CCNU), Semustine (methyl-CCNU) and Nimustine (ACNU)), ethylene imines and memyl-melamines (e.g., Thiotepa), folic acid analogs (e.g., Methotrexate), pyrimidine analogs (e.g., 5-Fluorouracil and Cytarabine), purine analogs (e.g., Mercaptopurine and Azathioprine), vinca alkaloids (e.g., Vinblastine, Nincristine and Vindesine), epipodophyllotoxins (e.g., Etoposide and Teniposide), antibiotics (e.g., Dactinomycin, Daunorubicin, Doxorubicin, Epirubicin, Bleomycin A2, Mitomycin C and Mitoxantrone), estrogens (e.g., Diethyl stilbestrol), gonadotropin-releasing hormon analogs (e.g., Leuprolide, Buserelin and Goserelin), antiestrogens (e.g., Tamoxifen and Ammoglutethimide), androgens (e.g., Testolactone and Drostanolonproprionate), and platinum complexes (e.g., Cisplatin and Carboplatin).

In one aspect, the therapeutic agent comprised in the particulate (e.g., a microparticle) or composition can be an anti-neoplastic agent. In particular embodiments, the therapeutic agent can be paclitaxel or derivative thereof, docetaxel or derivative thereof, or doxorubicin or derivative thereof. In certain aspects, entrapping the therapeutic agent in the particulate (e.g., a microparticle) does not substantially change the subject's responsiveness to a given amount of the therapeutic agent. In other aspects, the therapeutic agent can be a cytotoxic agent, and the subject's responsiveness can be measured by cytotoxicity of the cytotoxic agent. In other aspects, the method for treating a subject increases the tolerance dose of the subject to the therapeutic agent, compared to administering the therapeutic agent not entrapped in a particulate (e.g., a microparticle) of the present disclosure. In certain aspects, administering to the subject an effective amount of the particulate (e.g., a microparticle) or composition can reduce growth of neoplastic cells in the subject.

The present disclosure additionally provides a method for reducing tumor growth in a subject, comprising treating a subject in need thereof with an effective amount of radiation, and treating the subject with an effective amount of the particulate (e.g., a microparticle) or composition of any of the embodiments disclosed herein. In certain other aspects, provided herein is a method for reducing tumor growth in a subject, comprising treating a subject in need thereof with an effective amount of a chemotherapeutic agent, and treating the subject with an effective amount of the particulate (e.g., a microparticle) or composition of any of the embodiments disclosed herein. In yet other aspects, a method for reducing tumor growth in a subject is disclosed, the method comprising treating a subject in need thereof with an effective amount of a biologically active therapeutic agent, and treating the subject with an effective amount of the particulate (e.g., a microparticle) or composition of any of the embodiments disclosed herein.

In accordance with the method of the present disclosure, the individual therapy of a combination therapeutic strategy can be administered separately at different times during the course of therapy, in any suitable order, or concurrently in divided or single combination forms. For example, treatment with an effective amount of irradiation, a chemotherapeutic agent, or a biologically active therapeutic agent, or any combination thereof, can commence prior to, subsequent to or concurrent with commencement of treatment with an effective amount of the particulate (e.g., a microparticle) or composition of any of the embodiments disclosed herein. The instant disclosure is therefore to be understood as embracing all such regimes of simultaneous or alternating treatment and the term "administering" is to be interpreted accordingly.

The present disclosure additionally provides a method diagnosing a disease or condition using a particulate of the present disclosure. In some embodiments, the particulate useful for diagnosing a disease or condition includes a plurality of polysaccharide-vitamin conjugate and a diagnostic label. In some embodiments, the vitamin or analogue or derivative thereof in the conjugate is a targeting molecule that is capable of binding to a receptor in a tissue or a cell in a body (e.g., a tumor or a circulating blood cell). For example, a polysaccharide-folate conjugate may target folate receptor, which is highly overexpressed on the surface of many types of tumors. In some embodiments, the vitamin may be derivatized to include a targeting molecule such as a small molecule ligand, a peptide, or an antibody that binds to a receptor in a tissue or a cell in the body.

Examples of diagnostic labels include a radioactive isotope, an enzyme, a dye, a biotin, a fluorescent label and a chemiluminescent label. In some embodiments, the diagnostic method is an in vitro diagnostic method. Optionally, the method includes obtaining a sample from a subject (e.g., a tumor sample or a blood sample); contacting the sample with the present particulate; removing diagnostic labels that are not bound to a receptor in the sample; and determining the amount of the diagnostic labels bound to the receptor in the sample. In some embodiments, the diagnostic method is an in vivo imaging method. Optionally, the method includes administering the present particulate to a subject; detecting the presence of the diagnostic labels bound to a receptor in a subject. Optionally, the present of the diagnostic labels bound to a receptor in a subject is detected by an imaging device such as a magnetic resonance imaging device or an X-ray immunoscintigraphy imaging device, a positron emission tomography device, and the like.

The following examples are intended to further describe and illustrate various aspects of the disclosure, but not to limit, the scope of the disclosure in any manner, shape, or form, either explicitly or implicitly.

Example 1: Synthesis of Dextran-Folic Acid Conjugate

In this example, there are three steps for the synthesis of a dextran-folic acid conjugate.

Step (1): Synthesis of succinylated dextran. The synthetic route is shown in FIG. 1A and FIG. 1B.

18.0 g (0.33 mol OH) of dextran (T-70, Sigma Aldrich) was reacted at 80° C. with 33.0 g (0.33 mol) of succinic anhydride (Sigma Aldrich) using 900 mL of anhydrous N,N-dimethylformamide (DMF) (Sigma Aldrich) containing 20 mg/mL LiCl as solvent and 26.1 g (0.33 mol) of pyridine as catalyst. The reaction time was 30 hrs and the polymer was isolated by precipitation in cold 2M hydrochloride acid, washing with ice-cold water, dissolving in $NaHCO_3$ solution, precipitating the sodium salt in acetone, dissolving the polymer in water, re-precipitating in 2M hydrochloric acid, washing with ice-cold water, dissolving in acetone and finally precipitating in diethyl ether and drying to a stable weight.

Characterization of the functionalized dextran was carried out by IR and $^1H$ and $^{13}C$ NMR techniques. The degree of substitution (DS) was determined by means of titration for the modified polymer in dimethyl sulfoxide (DMSO) solution with 0.1 M sodium hydroxide in the presence of phenolphthalein. The polymer contained 85.0 mol % of ester groups (DS=2.55).

Step (2): Synthesis of amino folic acid. The synthetic route is shown in FIG. 1C.

Folic acid (3000 mg, 6.8 mmol) was dissolved in 120 mL of dry DMSO to which 858 mg (6.8 mmol) of DIC and 783 mg (6.8 mmol) of NHS were added. The reaction was left overnight at room temperature in the dark. Then, 1000 mL of acetone/ether (3:7) was added with stirring. The yellow precipitate FA-NHS ester was collected on sintered glass and washed with acetone/ether (3/7). The dried FA-NHS ester was used immediately in the next step of synthesis or put at −20° C. for storage.

2.78 g (50 mmol) of the dry FA-NHS ester was dissolved in 20 mL DMSO. 6.10 g (1000 mmol) of ethanediamine was immediately added into the above solution and incubated at room temperature (25° C.) for 12 hrs in dark with stirring. Then, 50 mL of acetone/ether (3/7) was poured into the solution with stirring. The yellow precipitate was collected and recrystallization in DMSO to obtain the purified amino folic acid.

Figure 1D:
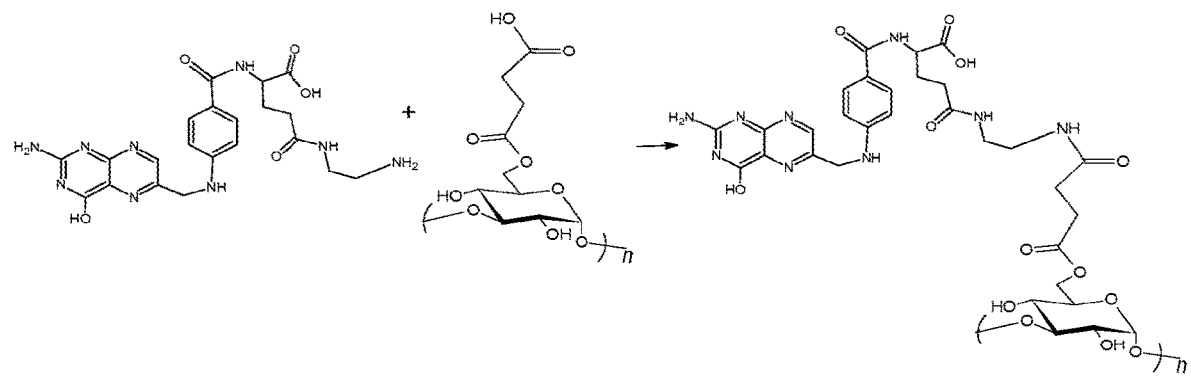
FIG. 1D is a schematic showing a reaction linking the products in FIG. 1B and FIG. 1C to form a dextran-folic acid conjugate.

Step (3): Synthesis of dextran-folic acid conjugate. The synthetic route is shown in FIG. 1D.

2000 mg of succinylated dextran (4.9 mmol saccharide unit) was dissolved in 40 mL of anhydrous DMF. 315.5 mg of DIC and 337.8 mg of HOBT was added and incubated for overnight at room temperature. Then, 473.8 mg amino Folic acid dissolved in 2 mL DMF was added and continued to stir for another 12 hours. The whole reactant was poured into Spectra/Por 3 dialysis bag (MW=3,500) and dialysis for 2 days. The solution was lyophilized to obtain a yellow solid. The final product was identified by 1H-NMR (d-DMSO): 2.8 (—$CH_2CH_2$—, Succinylated dextran), 3.2-3.6 (dextran), 4.4-5.8 (dextran), 8.6 (folic acid).

Example 2: Encapsulation of Paclitaxel with Dextran-Folic Acid Conjugate

In this example, the encapsulation process can be shown as the flow chart in FIG. 2.

1000 mg of dextran-folic acid conjugate was dissolved in 10 mL 20 mM PBS buffer (pH=7.4) and rotated on wheel until fully dissolved (5-10 minutes). Paclitaxel (300 mg) was dissolved in 1 mL Ethyl acetate/Benzyl alcohol (4:1) or $CH_2Cl_2$/Ethanol (4:1) and added to the above aqueous solution to obtain a crude formulation. Then, a high sheer homogenizer (LV1 Low Volume, Microfluidics Inc.) was applied to the crude emulsion at 30K Psi for 4-6 times. Afterward, the whole crude emulsion was poured into cold DI water under mixing at a ratio of 5:1 (water:emulsion). The solvent in the emulsion was finally removed by diafiltration to reach a final concentration of 100 mg/mL polymer. The particle size was measured and a 0.2 μm membrane was used to sterilize the formulation before lyophilization. A cyroprotectant, such as 10 wt % of sucrose was applied to keep the particle size during the following freezing-dry cycle.

Example 3: Freeze-Drying Process for the Lyo-Cake

In this example, a freeze-drying dosage form was designed for the formulation to increase its shelf lifetime. To obtain a lyo-cake with pharmaceutical elegant appearance, the above formulation produced in Example 2 was placed in a 30 mL serum vial and applied into a freezing-dryer (model: Virtis AdVantage Plus). The optimized cycle was shown as follows:

Freezing and annealing: Freeze to −40° C. for 120 min, raise the temperature to −22° C. for 90 min. Then, the temperature was dropped back to −40° C. and hold for 2 hours.

Primary drying process: The temperature rose back to −1° C. and continued hold under vacuum for 48.6 hrs.

Figure 3:
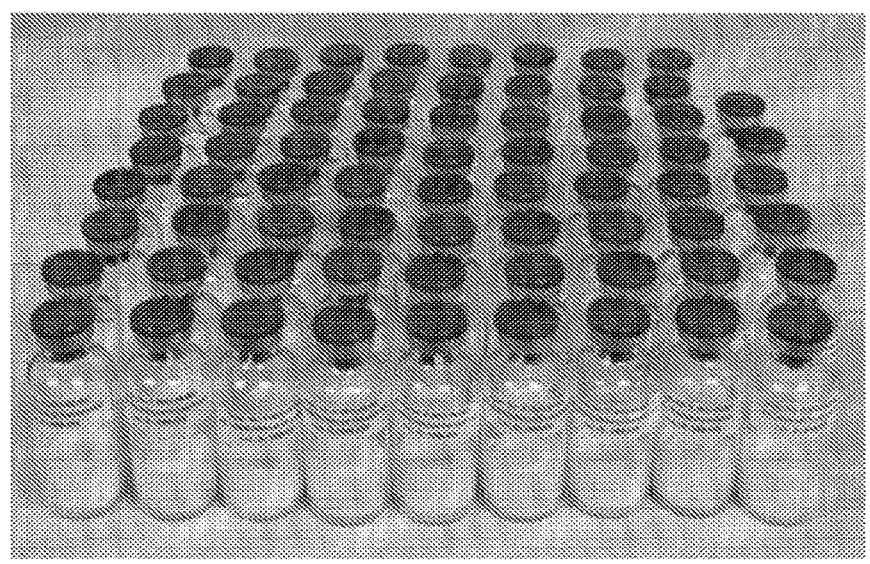
FIG. 3 shows vials containing a lyo-cake according to particular embodiments of the present disclosure.

Secondary drying process: Drying at 25° C. under vacuum for 7 hrs. The water content of the lyo-cake is less than 3.5% and final product was stored at a cool and dry storage room. The typical image of the vials is shown in FIG. 3.

The lyo-cake vial containing 300 mg paclitaxel was reconstituted within 3 minutes by 10 mL WFI to obtain a transparent bull liquid. The particle size was 120±20 nm measured by DLS, which showed the particulates (e.g., nanoparticles) did not aggregate after freeze-drying process. All of the physical-chemical characteristics for the lyo-cake are shown in Table 2.

TABLE 2

Physical-chemical characteristics of the lyo-cakes.

| Parameter | Test method | Specification (current) | Data |
|---|---|---|---|
| Appearance | Naked eyes | Yellow | Light yellow |
| Moisture content | KF | TBD (<5%) | 3.2% |
| Potency | RP-HPLC | TBD | 25.4 ± 1.0% |
| Impurities - Free DMAP | RP-HPLC | TBD (<1.0%) | 0.26 ± 0.01% |
| Reconstitution time | WFI and slight shaking | Dissolution | 2 min 30 sec |
| pH | pH meter | 7.4 ± 0.5 | 7.2 |
| Osmolarity | Osmometer | 290 ± 10 mOsm | 291 ± 2.4 |
| Particle size | DLS | <200 nm | 120 ± 20 nm |
| Particulates | Naked eyes | Particulate free | Particulate free |
| Endotoxin | LAL kinetic | <0.23 EU/mg | 0.18 EU/mg |

The accelerated stability was tested at 40° C. (100% Humidity) for 30 days. After reconstitution, the potency was compared with the material which was stored at ambient temperature. The assay was kept at 95-105%, which showed that the lyo-cake have at least one month shelf lifetime even under extreme conditions.

Example 4: In Vitro Evaluation for the Formulation

The lyo-cake containing paclitaxel was tested in vitro for cytotoxicity of human non-small lung cancer cells. After reconstitution with WFI, different concentrations of paclitaxel were placed on the cancer cells incubated with Gibco® cell culture medium for 72 hrs and the $IC_{50}$ was calculated according to the cell survival ratio. The results showed that the cytotoxicity of the entrapped paclitaxel was similar to paclitaxel itself without any treatment ($IC_{50} \approx 10$ nM). On the contrary, the dextran-folic acid (FA) conjugate did not show cytotoxicity with $IC_{50} > 0.05$ mg/mL. Therefore, the results showed the contribution of cytotoxicity comes from paclitaxel, not from the conjugate of dextran-FA.

Example 5: In Vivo Toxicity Evaluation for the Formulation

Figure 4A:
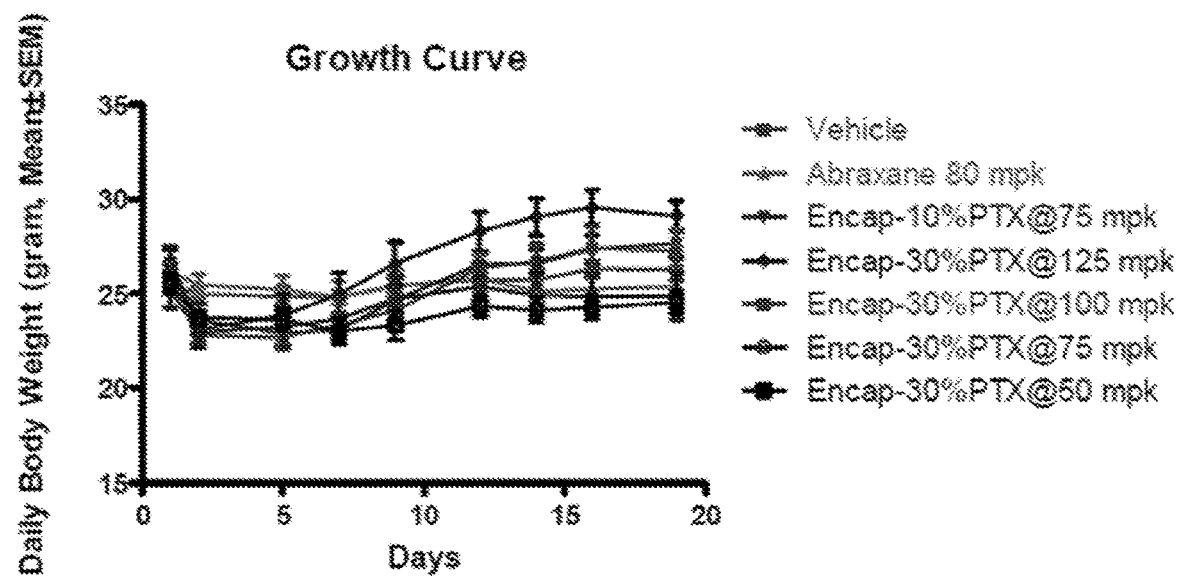
FIG. 4A illustrates in vivo toxicity evaluation based on body weight loss, for formulations according to certain embodiments of the present disclosure.

A comparison study was performed on C57/BL16 black mice for the toxicity of Abraxane® and the new formulation. The evaluation was based on the body weight loss and the maximum dose is defined as the body weight loss was less than 10%. According to FIG. 4A, the maximum dose for Abraxane® was 80 mg/kg Paclitaxel equivalence. However, the maximum dose for the new formulation was 125 mg/kg Paclitaxel equivalence. The results showed that the encapsulation of paclitaxel into the dextran-FA conjugate may reduce the toxicity of anti-cancer drug and increase the tolerance dose. Therefore, the formulation may be applied to a higher dosage in future clinic trial.

Example 6: Inhibition of Tumor Growth Using the Formulation

Figure 4B:
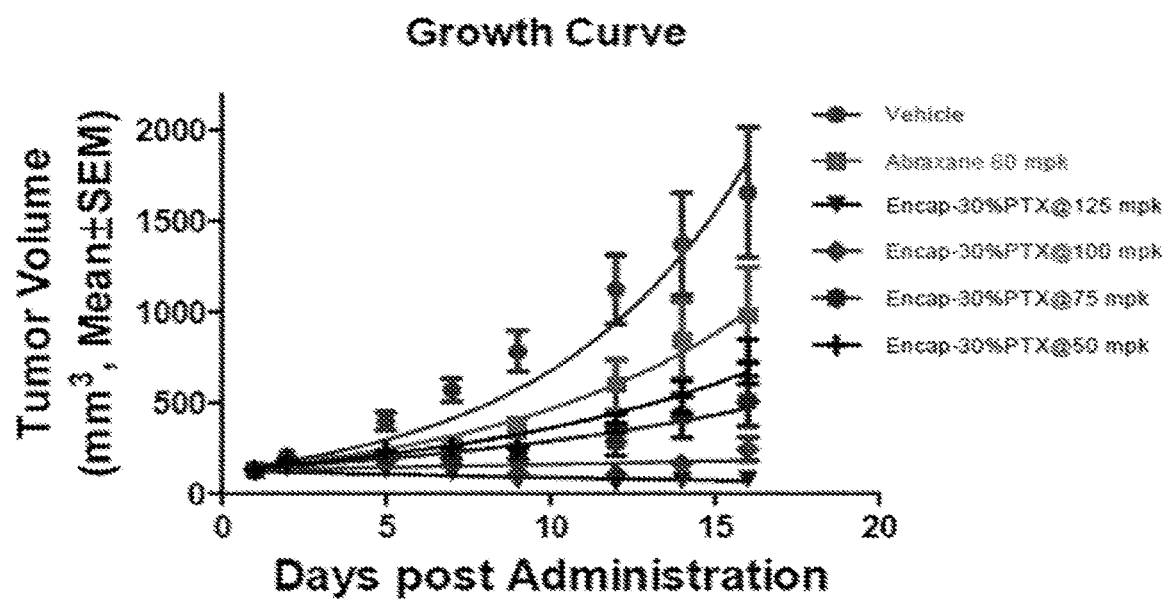
FIG. 4B shows anti-tumor activity of formulations according to certain embodiments of the present disclosure, using human non-small lung cancer cells in a xenograft model.

The anti-tumor activity was evaluated on Xenograft model planted with human non-small lung cancer cells. The reconstituted lyo-cake (paclitaxel/Polymer=30/100) were administrated through tail vein injection with the dose at 50, 75, 100, and 125 mg/kg paclitaxel equivalence. The control group was PBS, dextran-FA conjugate and Abraxane® (80 mg/kg paclitaxel equivalence). The inhibition of tumor growth was monitored and the results were shown in FIG. 4B. PBS and Dextran-FA conjugate did not have any tumor inhibition effect. However, the tumor growth inhibition for lyo-cake at 75 mg/kg (paclitaxel equivalence) was superior to Abraxane® at 80 mg/kg (paclitaxel equivalence), which was almost the same as lyo-cake at 50 mg/kg (paclitaxel equivalence).

According to the data, it can be concluded that the dextran-FA conjugate is non-toxic but can help the entrapped paclitaxel to inhibit tumor growth. In some aspect, the formulation is superior to the formulation on the market.

Example 7: Synthesis of Dextran-Folic Acid Conjugate

Figure 5A:
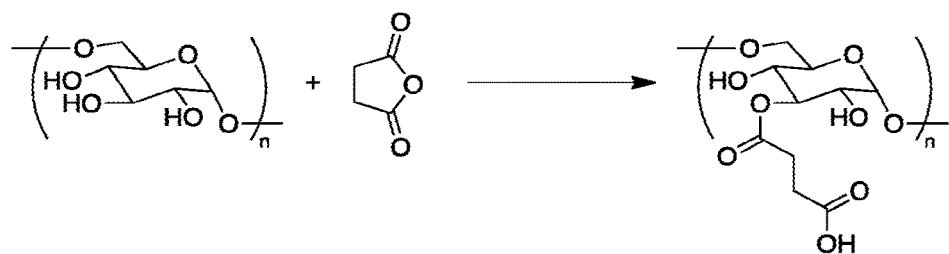
FIG. 5A is a schematic showing the synthesis of succinylated dextran.

Step 1: The modification of Dextran to Dextran-succinic acid. The synthetic route is shown in FIG. 5A.

To a 250 mL of RB was added dextran (40000 D, 30.0 g, 0.556 mol —OH) with 150 mL dimethyl sulfoxide anhydrous. The mixture was heated to 50° C. to obtain a clear solution. Followed by addition of succinic anhydride (5.01 g, 50.0 mmol) and 4-(dimethylamino)pyridine (150 mg, 1.23 mmol, 2.5% catalytic loading). The reaction mixture stirred vigorously for 24 hours. The result reaction mixture poured into 900 mL of cold absolute ethanol and white precipitates formed. The white solid was collected by centrifugation (4000 rpm, 4° C., 10 min). The resulting solid was dissolved in 300 mL water (pH 3.25) and added 30 mL of aqueous $NH_4HCO_3$ (0.10 M) to adjust the pH to neutral. The resulting aqueous solution was filtered through 0.2 μm PVDF filter (Whatman 6900-2502) then dialyzed against water with 10 mM $NH_4HCO_3$ for 4 days. Lyophilization to provide 18.4 g (53%) of Dextran-(succinic acid)$_{0.270}$.

Figure 5B:
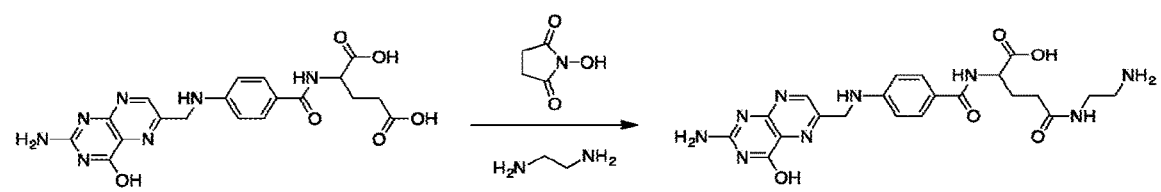
FIG. 5B is a schematic showing the synthesis of folic-NH—$CH_2CH_2$—$NH_2$.

Step 2: The modification of Folic acid with Ethylenediamine to Form Folic-NH—$CH_2CH_2$—$NH_2$. The synthetic route is shown in FIG. 5B.

To a 250 mL of RB was added folic acid (3.0 g, 6.8 mmol) with 80 mL dimethyl sulfoxide anhydrous. The mixture was heated to 50° C. to obtain a clear brown solution. Followed by addition of N,N'-Dicyclohexylcarbodiimide (930 mg, 4.5 mmol) in 20 mL dry DMSO and N-hydroxylsuccinimide (770 mg, 4.5 mmol) in 20 mL dry DMSO. The reaction mixture was stirred at room temperature for 20 hours. The dark brown reaction mixture turned turbid. The precipitates was removed by centrifugation (4000 rpm, 20° C., 10 min). The resulting clear dark brown solution was poured into 280 mL of 80/20 mix solvents of diethyl ether and acetone. The resulting tan precipitates were collected and washed (with 80/20 mix solvents of diethyl ether and acetone) by centrifugation (4000 rpm, 4° C., 10 min). The resulting tan semisolid was suspended in 50 mL water and lyophilized to 3.08 g of brown solid. The 3.08 g of brown solid was added to a 20-mL scintillation vial equipped with stirring bar with 12 mL of dry DMSO. To the mixture was added ethylenediamine (6.63 g, 7.4 mL) with vigorous stirring. The reaction mixture was capped and stirred for 18 hours. The resulting reaction mixture was poured into 80 mL of 80/20 mix solvents of diethyl ether and acetone. The brown precipitates were collected and washed (with 80/20 mix solvents of diethyl ether and acetone) by centrifugation (4000 rpm, 4° C., 10 min). The brown solid was recrystallized from dry DMSO (~10 mL). The brown solid from the DMSO recrystallization was collected and suspended in 30 mL water, lyophilized to give 3.04 g of product at 89%.

Figure 5C:
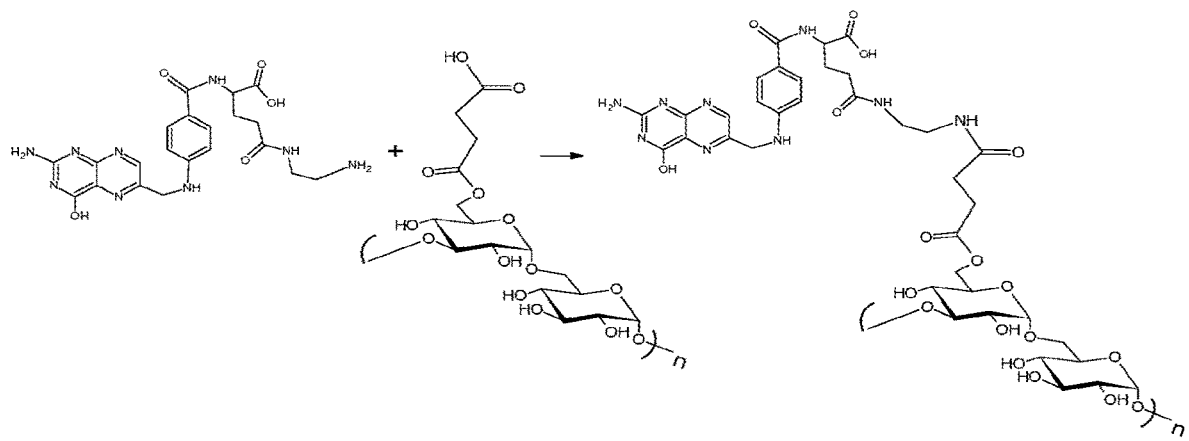
FIG. 5C is a schematic showing a conjugation reaction linking the products in FIG. 5A and FIG. 5B to form a conjugation of dextran-succinic acid with folic-NH—$CH_2CH_2$—$NH_2$.

Step 3: The conjugation of Dextran-succinic acid with Folic-NH—$CH_2CH_2$—$NH_2$. The synthetic route is shown in FIG. 5C.

To a 20-mL scintillation vial equipped with stirring bar was added Dextran-(succinic acid)$_{0.270}$ (source ZYT-WW- I-39, 1.0 g, 5.3 mmol glucose moiety, 1.42 succinic acid moiety) with 10 mL dimethyl sulfoxide anhydrous. The mixture was heated to 50° C. to obtain a clear solution. Followed by addition of N,N'-Dicyclohexylcarbodiimide (54.6. mg, 0.267 mmol, 5% eq of glucose moiety) and N-hydroxylsuccinimide (30.7 mg, 0.267 mmol, 1.05 eq) in 5 mL dry DMSO. The reaction mixture was stirred at room temperature for 20 hours. To the reaction mixture was added Folic-NH—$CH_2CH_2$—$NH_2$ (source ZYT-WW-I-45, 155 mg, 0.267 mmol) with 5 mL dry DMSO. The resulting reaction mixture was stirred at room temperature for additional 24 hours. The reaction mixture was poured into 80 mL cold absolute ethanol and light yellow precipitates formed. The light yellow solid was collected by centrifugation (6000 rpm, 10° C., 20 min). The resulting solid was dissolved in 30 mL water. The resulting aqueous solution was against dialyzed in water with 5 mM $NH_4HCO_3$ for 2 day, sonicated for 5 min, filtered through 0.2 μm PVDF filter (Whatman 6900-2502) then dialyzed against water with 6 mM $NH_4HCO_3$ for additional 1 days. The resulting clear solution is pH 7.0 and further dialyzed in water with 10 mM HOAc for 2 days. Brown solid formed inside the dialysis tube, the brown solid was collected by centrifugation (6000 rpm, 10° C., 20 min). The resulting brown paste was suspended in 50 mL water and lyophilized to provide 1.13 g of final product as light brown solid (yield 98%) as Dextran-(succinic acid)$_{0.22}$(succinic acid-NH—$CH_2CH_2$—NH-Folic)$_{0.05}$. UV-Vis spectra indicated the folic acid moiety is 3.8 mol % based on folic acid molar distinction coefficient. $^1$H NMR spectra indicated the folic acid moiety is ~3 mol % based on integration.

Example 8: The Modification of Cholic Acid with Ethylenediamine

Figure 6:
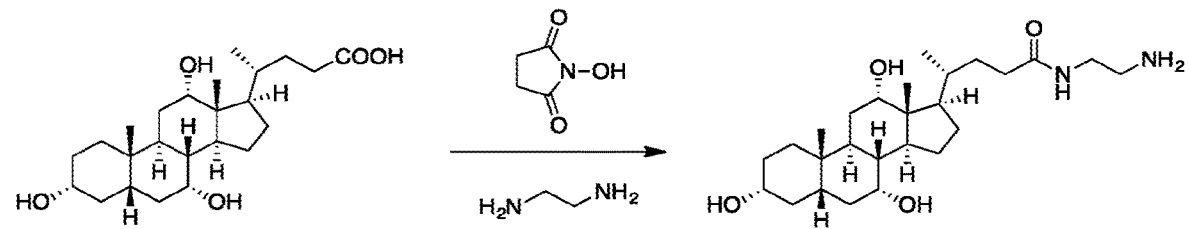
FIG. 6 is a schematic showing the modification of cholic acid with ethylenediamine.

The synthetic route is shown in FIG. 6. To a 20-mL scintillation vial equipped with stirring bar was added cholic acid (3.0 g, 7.34 mmol, 1.0 eq) with 10 mL dimethyl sulfoxide anhydrous. The mixture was heated to 50° C. to obtain a clear solution. Followed by addition of N,N'-Dicyclohexylcarbodiimide (1.59 g, 7.71 mmol, 1.05 eq) and N-hydroxylsuccinimide (890 mg, 7.7 mmol, 1.05 eq) in 10 mL dry DMSO. The reaction mixture was stirred at room temperature for 20 hours. To the reaction mixture was added ethylenediamine (6.63 g, 7.4 mL). The resulting reaction mixture was stirred at room temperature for additional 24 hours. The reaction mixture was poured into 80 mL of 80/20 mix solvents of ethanol and water. The resulting white precipitates were collected and washed (with 80/20 mix solvents of ethanol and water) by centrifugation (4000 rpm, 4° C., 10 min). The crude solid product was suspended in 50 mL water and lyophilized to 3.3 g of white solid (yield 100%).

Example 9: The Synthesis of Dextran-Succinic-NH—$CH_2CH_2$—NH-Cholic Acid

Figure 7:
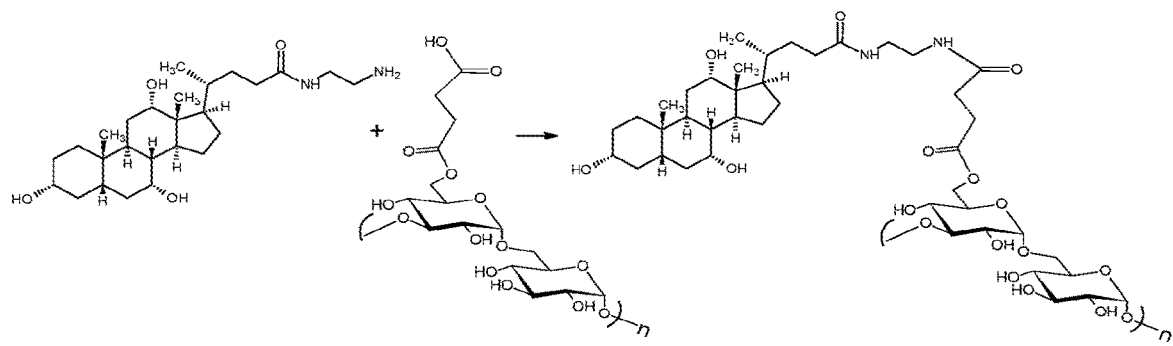
FIG. 7 is a schematic showing the synthesis of dextran-succinic-NH—CH$_2$CH$_2$—NH-cholic acid.

The synthetic route is shown in FIG. 7. A 20-mL scintillation vial equipped with stirring bar was added Dextran-(succinic acid)$_{0.270}$ (1.0 g, 5.3 mmol glucose moiety, 1.42 succinic acid moiety) with 10 mL dimethyl sulfoxide anhydrous. The mixture was heated to 50° C. to obtain a clear solution. Followed by addition of DCC (N,N'-Dicyclohexylcarbodiimide, 54.6. mg, 0.267 mmol, 5% eq of glucose moiety) and N-hydroxylsuccinimide (30.7 mg, 0.267 mmol, 1.05 eq) in 5 mL dry DMSO. The reaction mixture was stirred at room temperature for 20 hours. The reaction mixture was added Cholic-NH—$CH_2CH_2$—$NH_2$ (120 mg, 0.267 mmol) with 5 mL of dry DMSO. The resulting reaction mixture was stirred at room temperature for additional 24 hours. The reaction mixture was poured into 80 mL of cold absolute ethanol and off white precipitates were formed. The solid was collected by centrifugation (6000 rpm, 10° C., 20 min) and re-dissolved in 30 mL of water. The resulting aqueous solution was against dialyzed in water with 5 mM $NH_4HCO_3$ for 2 days, sonicated for 5 min, filtered through 0.2 μm PVDF filter (Whatman 6900-2502) then dialyzed against water with 6 mM $NH_4HCO_3$ for additional 1 days. The resulting clear solution is further dialyzed in water and lyophilized to provide 0.84 g (76% yield) of final product as off white solid as Dextran-(succinic acid)$_{0.22}$(succinic acid-NH—$CH_2CH_2$—NH-Cholic)$_{0.05}$.

Example 10: The Modification of Retinoic Acid with Ethylenediamine

Figure 8:
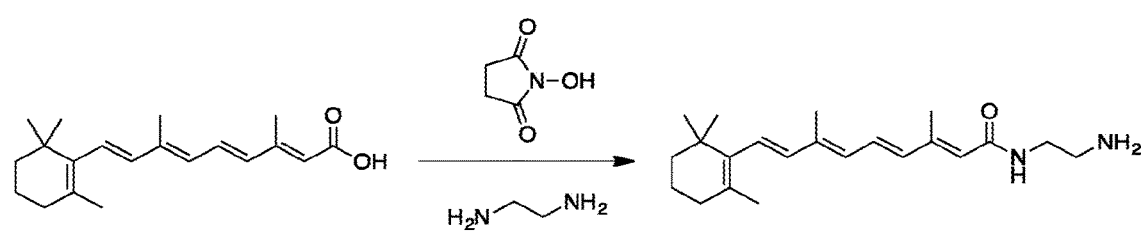
FIG. 8 is a schematic showing the modification of retinoic acid with ethylenediamine.

The synthetic route is shown in FIG. 8. To a 20-mL scintillation vial equipped with stirring bar was added retinoic acid (1.5 g, 5.0 mmol, 1.0 eq) with 10 mL dimethyl sulfoxide anhydrous. The mixture was heated to 50° C. to obtain a light yellow solution. Followed by addition of N,N'-Dicyclohexylcarbodiimide (1.08 g, 5.24 mmol, 1.05 eq) and N-hydroxylsuccinimide (603 mg, 5.24 mmol, 1.05 eq) in 10 mL dry DMSO. The reaction mixture was stirred at room temperature for 20 hours. To the reaction mixture was added ethylenediamine (3.3 g, 3.7 mL). The resulting reaction mixture was stirred at room temperature for additional 24 hours. The reaction mixture was poured into 80 mL of 80/20 mix solvents of ethanol and water. The resulting white precipitates were collected and washed (with 80/20 mix solvents of ethanol and water) by centrifugation (4000 rpm, 4° C., 10 min). The crude solid product was suspended in 50 mL water and lyophilized to 1.55 g of light yellow solid (yield 91%).

Example 11: The Synthesis of Dextran-Succinic-NH—$CH_2CH_2$—NH-Retinoic Acid

Figure 9:
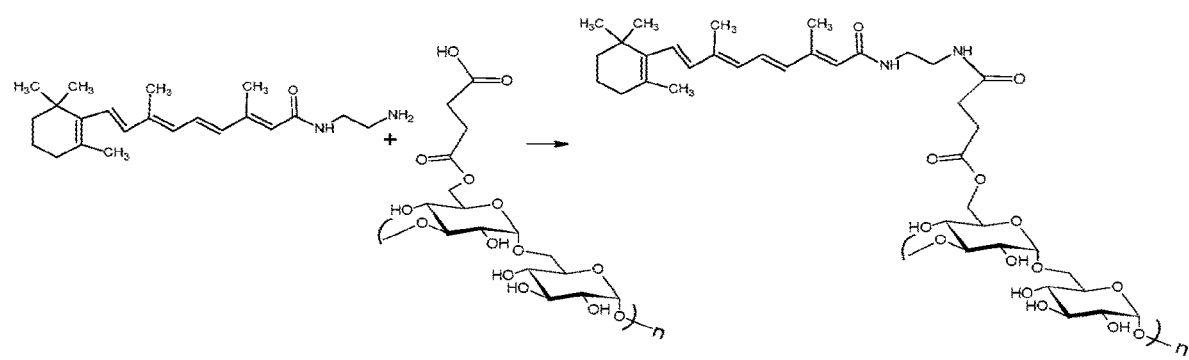
FIG. 9 is a schematic showing the synthesis of dextran-succinic-NH—CH2CH2-NH-retinoic acid.

The synthetic route is shown in FIG. 9. A 20-mL scintillation vial equipped with stirring bar was added Dextran-(succinic acid)$_{0.270}$ (1.0 g, 5.3 mmol glucose moiety, 1.42 succinic acid moiety) with 10 mL dimethyl sulfoxide anhydrous. The mixture was heated to 50° C. to obtain a clear solution. Followed by addition of DCC (N,N'-Dicyclohexylcarbodiimide, 54.6. mg, 0.267 mmol, 5% eq of glucose moiety) and N-hydroxylsuccinimide (30.7 mg, 0.267 mmol, 1.05 eq) in 5 mL dry DMSO. The reaction mixture was stirred at room temperature for 20 hours. To the reaction mixture was added Retinoic-NH—$CH_2CH_2$—$NH_2$ (91.5 mg, 0.32 mmol) with 5 mL dry DMSO. The resulting reaction mixture was stirred at room temperature for additional 24 hours. The reaction mixture was poured into 80 mL cold absolute ethanol and light yellow precipitates formed. The solid was collected by centrifugation (6000 rpm, 10° C., 20 min) and re-dissolved in 30 mL of water. The resulting aqueous solution was against dialyzed in water with 5 mM $NH_4HCO_3$ for 2 days, sonicated for 5 min, filtered through 0.2 μm PVDF filter (Whatman 6900-2502) then dialyzed against water with 6 mM $NH_4HCO_3$ for additional 1 days. The resulting clear solution is further dialyzed in water and lyophilized to provide 0.84 g (76% yield) of final product as white solid as light yellow solid as Dextran-(succinic acid)$_{0.22}$(succinic acid-NH—$CH_2CH_2$—NH-Retinoic)$_{0.05}$.

Example 12: The Synthesis of Dextran-Folic Acid-Cholic Acid Conjugate

Figure 10:
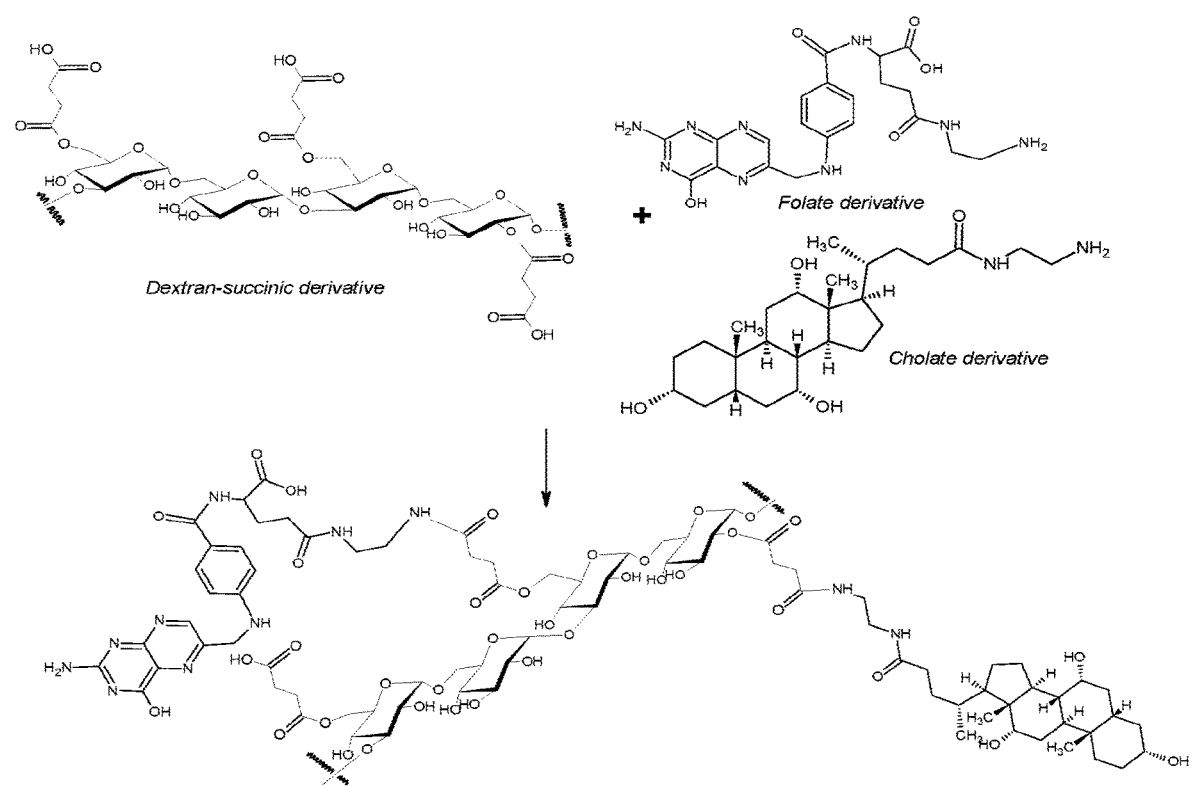
FIG. 10 is a schematic showing the synthesis of dextran-folic Acid-cholic Acid conjugate.

The synthetic route is shown in FIG. 10. A 200-mL RB flask equipped with stirring bar was added Dextran-(succinic acid)$_{0.270}$ (, 1.0 g, 5.3 mmol glucose moiety, 1.42 succinic acid moiety) with 15 mL dimethyl sulfoxide anhydrous. The mixture was heated to 50° C. to obtain a clear solution. Followed by addition of DCC (N,N'-Dicyclohexylcarbodiimide, 110 mg, 0.534 mmol, 10% eq of glucose moiety) and N-hydroxysuccinimide (61 mg, 0.534 mmol) in 5 mL dry DMSO. The reaction mixture was stirred at room temperature for 24 hours. A solution of Folic-NH—$CH_2CH_2$—$NH_2$ (465 mg, 0.96 mmol) in 5 mL dry DMSO and a solution of Cholic-NH—$CH_2CH_2$—$NH_2$ (120 mg, 0.267 mmol) in 5 mL dry DMSO were prepared and mixed. The resulting mix of DMSO solution was added to the reaction mixture with vigorous stirring at room temperature, and continued stirring for additional 24 hours. The reaction mixture was poured into 80 mL cold absolute ethanol and light yellow precipitates formed. The light yellow solid was collected by centrifugation (6000 rpm, 10° C., 20 min). The resulting solid was dissolved in 30 mL water. The resulting aqueous solution was against dialyzed in water with 5 mM $NH_4HCO_3$ for 2 days, sonicated for 5 min, filtered through 0.2 μm PVDF filter (Whatman 6900-2502) then dialyzed against water with 6 mM $NH_4HCO_3$ for additional 1 days. The resulting clear solution is dialyzed in water for 2 days and lyophilized to provide ~1.0 g (yield 74%) of light brown solid as Dextran-(succinic acid)$_{0.17}$(succinic-NH—$CH_2CH_2$—NH-Folic)$_{0.05}$(succinic-NH—$CH_2CH_2$—NH-Cholic)$_{0.05}$.

Figure 11:
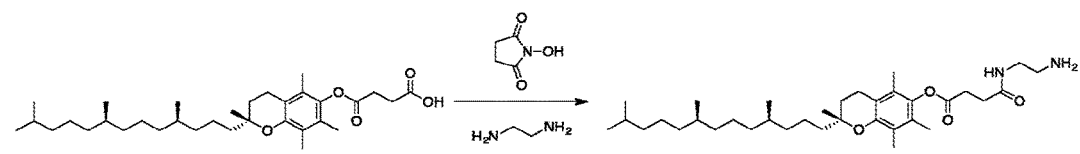
FIG. 11 is a schematic showing the modification of tocopherol succinic acid with ethylenediamine.

Example 13: The Modification of Tocopherol Succinic Acid with Ethylenediamine The synthetic route is shown in FIG. 11. To a 20-mL scintillation vial equipped with stirring bar was added tocopherol succinic acid (3.0 g, 5.65 mmol, 1.0 eq) with 10 mL dimethyl sulfoxide anhydrous. The mixture was heated to 50° C. to obtain a clear solution. Followed by addition of N,N'-Dicyclohexylcarbodiimide (1.22 g, 5.93 mmol, 1.05 eq) and N-hydroxysuccinimide (682 mg, 5.93 mmol, 1.05 eq) in 10 mL dry DMSO. The reaction mixture was stirred at room temperature for 20 hours. To the reaction mixture was added ethylenediamine (6.63 g, 7.4 mL). The resulting reaction mixture was stirred at room temperature for additional 24 hours. The reaction mixture was poured into 80 mL of 80/20 mix solvents of ethanol and water. The resulting white precipitates were collected and washed (with 80/20 mix solvents of ethanol and water) by centrifugation (4000 rpm, 4° C., 10 min). The crude solid product was suspended in 50 mL water and lyophilized to 2.94 g of white solid (yield 60%).

Example 14: Encapsulation of Paclitaxel with Dextran-Folic Acid Conjugate by Water Miscible Solvent 420 mg of dextran-folic acid conjugate was dissolved in 70 mL water and stirred until fully dissolved (5-10 minutes). Paclitaxel (100 mg) was dissolved in 3.5 mL Ethanol and added to the above aqueous solution mixing by a rotor-stator for 2 minutes at 8,000 psi forming a premix. Then, a high sheer homogenizer (M110P, Microfluidics Inc.) was applied to the crude emulsion at 29K Psi for 1-5 times. Afterward, the ethanol was evaporated from the crude emulsion under a reduced pressure at room temperature. The particle size was measured and a 0.22 μm membrane was used to sterilize the formulation before lyophilization. A cyroprotectant, such as 10 wt % of sucrose was applied to keep the particle size during the following freezing-dry cycle.

Example 15: Encapsulation of Paclitaxel with Dextran-Cholic Acid, Dextran-Retinoic Acid or Dextran-Folic-Cholic Acid Conjugate by Water Miscible Solvent 420 mg of polymer was dissolved in 70 mL water and stirred until fully dissolved (5-10 minutes). Paclitaxel (100 mg) was dissolved in 3.5 mL Ethanol and added to the above aqueous solution mixing by a rotor-stator for 2 minutes at 8,000 psi forming a premix. Then, a high sheer homogenizer (LM20, Microfluidics Inc.) was applied to the crude emulsion at 29K Psi for 1-5 times. Afterward, the ethanol was evaporated from the crude emulsion under a reduced pressure at room temperature. The particle size was controlled between 100-200 nm and a 0.22 μm membrane was used to sterilize the formulation before lyophilization. A cyroprotectant, such as 10 wt % of sucrose was applied to keep the particle size during the following freezing-dry cycle.

Example 16: Stability of Reconstituted Particulate Solution

A lyophilized particulate sample having dextran-folic acid conjugate and encapsulated paclitaxel prepared in Example 2 is reconstituted in sterile, pyrogen-free aqueous solution. The reconstituted sample was kept at room temperature (23° C.-35° C.) for 10 days. The reconstituted sample was analyzed at day 1, day 7, and day 10, respectively, using chromatography. Drug concentrations and purity remain the same at day 7 and day 10 as compared to those at day 1. Particle sizes at day 1, day 7, and day 10 are also analyzed, and were shown to remain in a same range.

All headings are for the convenience of the reader and should not be used to limit the meaning of the text that follows the heading, unless so specified.

Citation of the above publications or documents is not intended as an admission that any of them is pertinent prior art, nor does it constitute any admission as to the contents or date of these publications or documents.

While various embodiments of the present disclosure have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

What is claimed is:

1. A non-micelle particulate, comprising:
a plurality of polysaccharide-vitamin conjugates; and
an active agent encapsulated in the plurality of polysaccharide-vitamin conjugates;
wherein a respective one of the plurality of polysaccharide-vitamin conjugates comprises:
a polysaccharide molecule; and
one or more molecules of vitamin, or analogue or derivative that retains biological function and activity of the vitamin,
wherein each of the one or more molecules of vitamin, or analogue or derivative that retains biological function and activity of the vitamin, is covalently conjugated to the polysaccharide molecule through a linker group comprising at least two atoms;
the linker group is exogenous to the polysaccharide molecule and bonds to a monomeric ring of the polysaccharide molecule;
wherein a surface of the particulate is hydrophilic;
at least one of the plurality of molecules of vitamin, or analogue or derivative that retains biological function and activity of the vitamin is encapsulated in an inner portion of the non-micelle particulate; and
the active agent is encapsulated in the inner portion of the non-micelle particulate and is non-covalently bound to the at least one of the plurality of molecules of vitamin, or analogue or derivative that retains biological function and activity of the vitamin, in the inner portion of the non-micelle particulate.

2. The non-micelle particulate of claim 1, wherein active agent molecules are encapsulated throughout the inner portion of the non-micelle particulate.

3. The particulate of claim 1, wherein active agent molecules are randomly encapsulated throughout the inner portion of the non-micelle particulate, and do not segregate inside an inner core of the particulate.

4. The non-micelle particulate of claim 1, wherein the polysaccharide molecule is conjugated to the vitamin, or analogue or derivative that retains biological function and activity of the vitamin, through a linker molecule comprising a first chemical group reactive to one or more functional groups on the polysaccharide molecule or a functionalized polysaccharide molecule, and a second chemical group reactive to one or more functional groups on the vitamin, or analogue or derivative that retains biological function and activity of the vitamin, or a functionalized molecule thereof.

5. The non-micelle particulate of claim 1, wherein the polysaccharide-vitamin conjugate comprises a first vitamin, or analogue or derivative that retains biological function and activity of the first vitamin, and a second vitamin, or analogue or derivative that retains biological function and activity of the second vitamin;
wherein the second vitamin, or analogue or derivative that retains biological function and activity of the second vitamin is different from the first vitamin, or analogue or derivative that retains biological function and activity of the first vitamin;
the first vitamin, or analogue or derivative that retains biological function and activity of the first vitamin, is covalently linked to the polysaccharide at a first position of the polysaccharide;
the second vitamin, or analogue or derivative that retains biological function and activity of the second vitamin, is covalently linked to the polysaccharide at a second position of the polysaccharide, the second position being different from the first position; and
the active agent is non-covalently bound to the first vitamin, or analogue or derivative that retains biological function and activity of the first vitamin, or the second vitamin, or analogue or derivative that retains biological function and activity of the second vitamin, or both.

6. The non-micelle particulate of claim 1, wherein the one or more molecules of vitamin, or analogue or derivative that retains biological function and activity of the vitamin is folate, nicotinamide, N,N-diethylnicotinamide, or biotin.

7. The non-micelle particulate of claim 1, wherein the polysaccharide is a polysaccharide soluble in water and in an organic solvent.

8. The non-micelle particulate of claim 5, wherein the polysaccharide is dextran or derivative thereof, cellulose or derivative thereof, carboxymethylcellulose, or hyaluronic acid or derivative thereof.

9. The non-micelle particulate of claim 1, wherein the polysaccharide is succinylated, carboxymethylated, and/or modified by cyclic anhydride.

10. The non-micelle particulate of claim 1, wherein the one or more molecules of vitamin, or analogue or derivative that retains biological function and activity of the vitamin, are hydrophobic.

11. The non-micelle particulate of claim 1, wherein the active agent is hydrophobic.

12. The non-micelle particulate of claim 1, wherein the active agent is an anti-neoplastic agent.

13. The non-micelle particulate of claim 1, wherein the active agent is a taxane compound or a camptothecin compound.

14. The non-micelle particulate of claim 1, wherein an average diameter of the non-micelle particulate is between about 20 nm and about 1000 nm.

15. A pharmaceutical composition comprising the non-micelle particulate of claim 1, and a pharmaceutically acceptable carrier or excipient.

16. A method for treating a patient, comprising administering to the patient an effective amount of the composition of claim 15.

17. A method for inhibiting growth of a cell, comprising delivering to a cell an effective amount of the composition of claim 15.

18. A method for reducing tumor growth in a subject, comprising treating a subject in need thereof with an effective amount of radiation, and treating the subject with an effective amount of the composition of claim 15.

19. A method for reducing tumor growth in a subject, comprising treating a subject in need thereof with an effective amount of a chemotherapeutic agent, and treating the subject with an effective amount of the composition of claim 15.

20. A method for reducing tumor growth in a subject, comprising treating a subject in need thereof with an effective amount of a biologically active therapeutic, and treating the subject with an effective amount of the composition of claim 15.

21. The non-micelle particulate of claim 1, wherein one or more molecules of vitamin, or analogue or derivative that retains biological function and activity of the vitamin do not segregate into a distinct layer; and
a bi-layer structure is substantially absent in the non-micelle particulate.

22. The non-micelle particulate of claim 1, wherein the inner portion of the non-micelle particulate has a substantially homogeneous structure.

23. The non-micelle particulate of claim 1, wherein a molar ratio of the one or more molecules of vitamin, or analogue or derivative that retains biological function and activity of the vitamin to the polysaccharide molecule is in a range of 1:40 to 2:1.

24. The non-micelle particulate of claim 1, wherein the non-micelle particulate has a loading capacity in a range of 10% to 30%.

* * * * *